(12) United States Patent
Bös et al.

(10) Patent No.: US 6,194,410 B1
(45) Date of Patent: Feb. 27, 2001

(54) PYRAZOLOPYRIMIDINE AND PYRAZOLINES AND PROCESS FOR PREPARATION THEREOF

(75) Inventors: Michael Bös, Rheinfelden (CH); Claus Riemer, Freiburg (DE); Heinz Stadler, Rheinfelden (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/256,927

(22) Filed: Feb. 24, 1999

(30) Foreign Application Priority Data

Mar. 11, 1998 (EP) .................................. 98104346

(51) Int. Cl.$^7$ ................... A01N 43/64; A61K 31/505; C07D 251/00; C07D 487/00
(52) U.S. Cl. ................... 514/246; 514/258; 544/215; 544/263; 544/281
(58) Field of Search .................. 544/263, 281, 544/215; 514/258, 246

(56) References Cited

U.S. PATENT DOCUMENTS 5,571,813 * 11/1996 Ruhter et al. .................. 514/257

FOREIGN PATENT DOCUMENTS

| 38 25 043 | 2/1990 | (DE) . |
|---|---|---|
| 0 301 919 | 2/1989 | (EP) . |
| WO 97/11075 | 3/1997 | (WO) . |
| WO 98/27058 | 6/1998 | (WO) . |
| WO 98/27081 | 6/1998 | (WO) . |
| WO 99/02502 | 1/1999 | (WO) . |

OTHER PUBLICATIONS

W.E. Kirkpatrick et al., Journal of Medicinal Chemistry, vol. 20, No. 3, p. 386–393 (1997).
Abstract of DE 3825043, WPI Acc. No. 99–052252/199008, 1990.
A. Bourson et al., The Journal of Pharmacology and Experimental Therapeutics, 274(1):173–180 (1995).
B. Roth et al., The Journal of Pharmacology and Experimental Therapeutics, 268(3):1403–1410 (1994).
F. Monsma et al., Molecular Pharmacology, 43:320–327 (1993).
A. Sleight et al., Neurotransmissions, 11(3):1–5 (1995).
R. Ward et al., Neuroscience, 64(4):1105–1111 (1995).

\* cited by examiner

*Primary Examiner*—Mukund J. Shah
*Assistant Examiner*—Tamthom N. Truong
(74) *Attorney, Agent, or Firm*—George W. Johnston; Patricia S. Rocha-Tramaloni; Eileen M. Ebel

(57) ABSTRACT

The present invention is concerned with pyrazolopyrimidines and pyrazolotriazines of the general formula

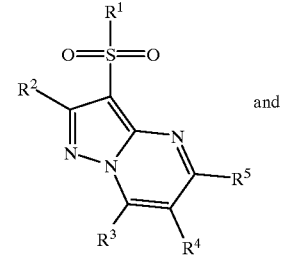

I-A

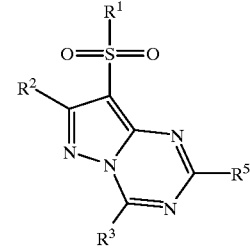

I-B and their pharmaceutically acceptable salts.

Surprisingly, these compounds evidence selective affinity to 5HT-6 receptors. They are accordingly suitable for use in the treatment and prevention of central nervous disorders such as, for example, psychoses, schizophrenia, manic depressions, depressions, neurological disorders, memory disorders, Parkinson's disease, amyotrophic lateral sclerosis, Alzheimer's disease and Huntington's chorea.

12 Claims, No Drawings

PYRAZOLOPYRIMIDINE AND PYRAZOLINES AND PROCESS FOR PREPARATION THEREOF

FIELD OF THE INVENTION

The present invention is relates to pyrazolopyrimidines and pyrazolo-triazines of the general formula

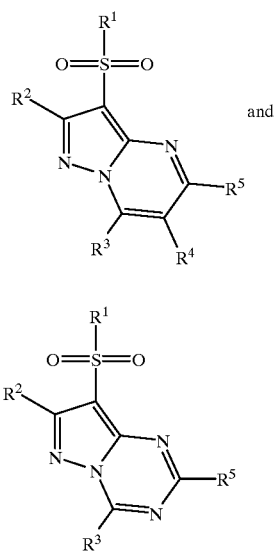

wherein
- $R^1$ is phenyl, optionally substituted by one or more lower alkyl, halogen or lower alkoxy; tolyl; pyridyl; naphthyl; or thiophenyl;
- $R^2$ is hydrogen; lower alkyl; lower thioalkyl; or hydroxy-lower-alkoxy;
- $R^3$ is amino; lower alkylamino; di-lower-alkyl-amino; piperazinyl, optionally substituted by one or more lower alkyl, benzyl, phenyl or hydroxy-lower-alkyl; morpholinyl; imidazolyl; $(CH_3)_2N(CH_2)_nNH—$; $(CH_3)_2N(CH_2)_nO—$ or morpholinyl—$(CH_2)_nO—$ in which n signifies 2 or 3;
- $R^4$ is hydrogen; lower alkyl; or hydroxy-lower-alkyl;
- $R^5$ is hydrogen; halogen; lower alkyl; $C_3$–$C_6$-cycloalkyl; lower alkyl-lower-alkoxy; hydroxy-lower-alkyl-lower-alkoxy; $(CH_3)_2N(CH_2)_nNH—$; piperazinyl, optionally substituted by lower alkyl; methyl-piperazinyl, optionally substituted by lower alkyl; morpholinyl; methyl-morpholinyl; di-lower-alkylamino; or di-lower-alkylamino-lower-alkyl; or
- $R^4$ and $R^5$ together represent $—(CH_2)_m—$ or $—CH_2—S—CH_2—$ wherein m is 3 or 4, and their pharmaceutically acceptable salts.

BACKGROUND OF THE INVENTION

These compounds surprisingly evidence a selective affinity to 5HT-6 receptors. They are accordingly suitable for use in the treatment and prevention of central nervous disorders such as, for example, psychoses, schizophrenia, manic depressions (Bryan L. Roth et al., J. Pharmacol. Exp. Ther., 268, pages 1403–1410 (1994)), depressions (David R. Sibley et al., Mol. Pharmacol., 43, pages 320–327 (1993)), neurological disorders (Anne Bourson et al., J. Pharmacol. Exp. Ther., 274, pages 173–180 (1995); R. P. Ward et al., Neuroscience, 64, pages 1105–1110 (1995)), memory disorders, Parkinson's disease, amyotrophic lateral sclerosis, Alzheimer's disease and Huntington's chorea (Andrew J. Sleight et al., Neurotransmissons, 11, pages 1–5 (1995)).

Preferred is the treatment of Alzheimer's disease.

Objects of the present invention are the novel compounds of formula I-A and I-B and their pharmaceutically useable salts, the use of these compounds as therapeutically active substances, the manufacture of these compounds, medicaments containing one or more of these compounds, optionally in the form of one of their pharmaceutically useable salts, as well as the production of such medicaments.

Preferred compounds of general formula I-A are those in which $R^3$ represents amino, such as, for example 3-benzenesulphonyl-5-methyl-2-methylsulphanyl-pyrazolo[1,5-a]pyrimidin-7-ylamine, 3-(4-isopropyl-benzenesulphonyl)-5-methyl-2-methylsulphanyl-pyrazolo[1,5-a]-pyrimidin-7-ylamine, 5-methyl-2-methylsulphanyl-3-(naphthalene-2-sulphonyl)-pyrazolo[1,5-a]pyrimidin-7-ylamine, 3-(4-fluoro-benzenesulphonyl)-5-methyl-2-methylsulphanyl-pyrazolo[1,5-a]pyrimidin-7-ylamine, 3-benzenesulphonyl-5-cyclopropyl-2-methylsulphanyl-pyrazolo[1,5-a]pyrimidin-7-ylamine, 3-benzenesulphonyl-2-methylsulphanyl-6,7-dihydro-5H-cyclopenta[d]pyrazolo[1,5-a]pyrimidin-8-ylamine, 3-benzenesulphonyl-5-isopropyl-2-methylsulphanyl-pyrazolo[1,5-a]pyrimidin-7-ylamine, 5-methyl-2-methylsulphanyl-3-(toluene-2-sulphonyl)-pyrazolo[1,5-a]pyrimidin-7-ylamine, 5-methyl-2-methylsulphanyl-3-(toluene-3-sulphonyl)-pyrazolo[1,5-a]pyrimidin-7-ylamine, 3-benzenesulphonyl-5-methoxymethyl-2-methylsulphanyl-pyrazolo[1,5-a]pyrimidin-6-ylamine, 3-benzenesulphonyl-N5,N5-dimethyl-2-methylsulphanyl-pyrazolo[1,5-a]pyrimidin-5,7-diamine, 3-benzenesulphonyl-N5-(2-dimethylamino-ethyl)-2-methylsulphanyl-pyrazolo[1,5-a]pyrimidin-5,7-diamine, 3-benzenesulphonyl-5-(4-methyl-piperazin-1-yl)-2-methylsulphanyl-pyrazolo[1,5-a]pyrimidin-7-ylamine and 3-benzenesulphonyl-5-dimethylaminomethyl-2-methylsulphanyl-pyrazolo[1,5-a]pyrimidin-7-ylamine.

Additionally preferred, compounds of formula I-A are those in which $R^3$ represents piperazinyl, such as, for example, 3-benzenesulphonyl-5-methyl-2-methylsulphanyl-7-piperazin-1-yl-pyrazolo[1,5-a]pyrimidine, 3-(4-tert-butyl-benzenesulphonyl)-5-methyl-2-methylsulphanyl-7-piperazin-1-yl-pyrazolo[1,5-a]pyrimidine, 3-benzenesulphonyl-5,6-dimethyl-2-methylsulphanyl-7-piperazin-1-yl-pyrazolo-[1,5-a]pyrimidine, 3-benzenesulphonyl-2-methylsulphanyl-7-piperazin-1-yl-5-propyl-pyrazolo[1,5-a]pyrimidine, 3-benzenesulphonyl-5-cyclopropyl-2-methylsulphanyl-7-piperazin-1-yl-pyrazolo[1,5-a]pyrimidine, 3-benzenesulphonyl-2-methylsulphanyl-8piperazin-1-yl-6,7-dihydro-5H-cyclo-penta[d]pyrazolo[1,5-a]pyrimidine, 3-benzenesulphonyl-2-methylsulphanyl-8-piperazin-1-yl-5H,7H-pyrazolo[1,5-a]thieno[3,4-d]pyrimidine, 5-methyl-2-methylsulphanyl-7-piperazin-1-yl-3-(thiophen-2-sulphonyl)-pyrazolo[1,5-a]pyrimidine, 3-benzenesulphonyl-2-ethyl-8-piperazin-1-yl-6,7-dihydro-5H-cyclopenta[d]pyrazolo[1,5-a]pyrimidine and 5-methyl-2-methylsulphanyl-7-piperazin-1-yl-3-(toluol-2-sulphonyl)-pyrazolo[1,5-a]pyrimidine.

Furthermore, there are preferred compounds of formula I-A and I-B in which $R^3$ represents methylpiperazinyl, such as, for example, 3-benzenesulphonyl-5-cyclopropyl-2-methylsulphanyl-7-(4-methylpiperazin-1-yl) -pyrazolo[1,5-a]pyrimidine, 3-benzenesulphonyl-8-(4-methyl-piperazin-1-yl)-2-methylsulphanyl-6,7-dihydro-5H-cyclopenta[d]pyrazolo[1,5-a]pyrimidine, 3-benzenesulphonyl-8-(4-methyl-piperazin-1-yl)-2-methylsulphanyl-5H,7H-pyrazolo[1,5-a]thieno[3,4-d]pyrimidine, 3-benzenesulphonyl-5-isopropyl-7-(4-methyl-piperazin-1-yl)-2-methylsulphanyl-pyrazolo[1,5-a]pyrimidine and 2-[3-benzenesulphonyl-7-(4-methyl-piperazin-1-yl)-2-methylsulphanyl-pyrazolo-[1,5-a]pyrimidine-5-yloxy]-ethanol.

8-Benzenesulphonyl-7-methylsulphanyl-pyrazolo[1,5-a][1,3,5]triazin-4-ylamine and 8-benzenesulphonyl-2-methyl-4-(4-methylpiperazin-1-yl)-7-methylsulphanyl-pyrazolo[1,5-a][1,3,5]triazine are other preferred triazines of general formula I-B.

The term "lower alkyl" as used in the present description denotes residues from 1 to 7, preferably from 1 to 4, carbon atoms, such as, for example, methyl, ethyl, n-propyl, i-propyl, n-butyl, i-butyl and t-butyl.

The term "lower alkoxy" denotes a lower alkyl residue in the sense of the foregoing definition bonded via an oxygen atom, such as, for example, methoxy, ethoxy, n-propoxy, i-propoxy, n-butoxy, i-butoxy and t-butoxy.

The term "lower alkylamino" denotes a lower alkyl residue in the sense of the foregoing definition bonded via an NH group, such as, for example, methylamino and ethylamino.

The term "di-lower-alkylamino" represents identical or different lower alkyl residues in the sense of the foregoing definition bonded via a nitrogen atom, such as, for example, dimethylamino, diethylamino or methyl-ethyl-amino.

The term "halogen" includes fluorine, chlorine, bromine and iodine.

The term "lower thioalkyl" denotes a lower alkyl residue in the sense of the foregoing bonded via a sulphur atom.

The preparation of the novel compounds can be effected in a manner known to one skilled in the art. Specifically, compounds of formula I-A may be synthesized as is described in Examples 1–123. Compounds of formula I-B maybe synthesized as is described in Examples 124–129. Furthermore, Schemes 1–3 provide a general overview with respect to the alternatives available for the preparation of these novel compounds, the starting compounds of formula III in Scheme 1 being prepared in a manner analogous to described methods.

The compounds of formula I-A and I-B also include those compounds in which hydrogen can be replaced by tritium.

DETAILED DESCRIPTION OF THE INVENTION

The compounds of formula I-A and I-B can be prepared by reacting a compound of the formula

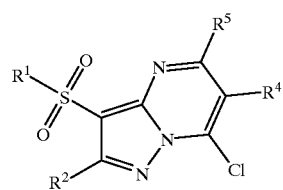

X or a compound of the formula

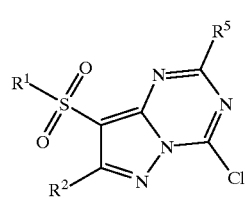

XIV with a compound of the formula

HR³ wherein $R^1$—$R^5$ are as described above. Optionally these compounds may be converted into a pharmaceutically acceptable salt.

The reaction of a compound of formula X or XIV with a compound of the formula HR³ is effected according to known methods. Conveniently, a compound of formula X or XIV is dissolved in DMF and depending on the reaction partner, which can be dissolved in DMF or an alcohol, reacted at room temperature or at the boiling temperature of the solvent used. Especially preferred reaction partners for the compounds of formula X or XIV are piperazine, 1-methyl-piperazine, NH₃, methylamine, dimethyl-amine, morpholine, imidazole, N-benzylpiperidine, 1-(2-hydroxyethyl)-piperazine, 1-phenylpiperazine, 2-dimethylaminoethylamine or cis-2,6-dimethylpiperazine.

The compounds of formula I-A and I-B can subsequently converted into pharmaceutically acceptable salts, such as salts with inorganic or organic acids. Examples from the large number of such salts are hydrochlorides, hydrobromides, sulphates, nitrates, citrates, acetates, maleates, succinates, methanesulphonates, p-toluenesulphonates and the like. These salts may be prepared according to known methods which will be familiar to those skilled in the art.

Scheme 1

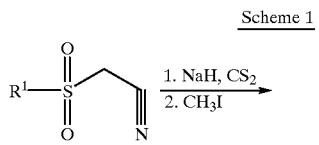

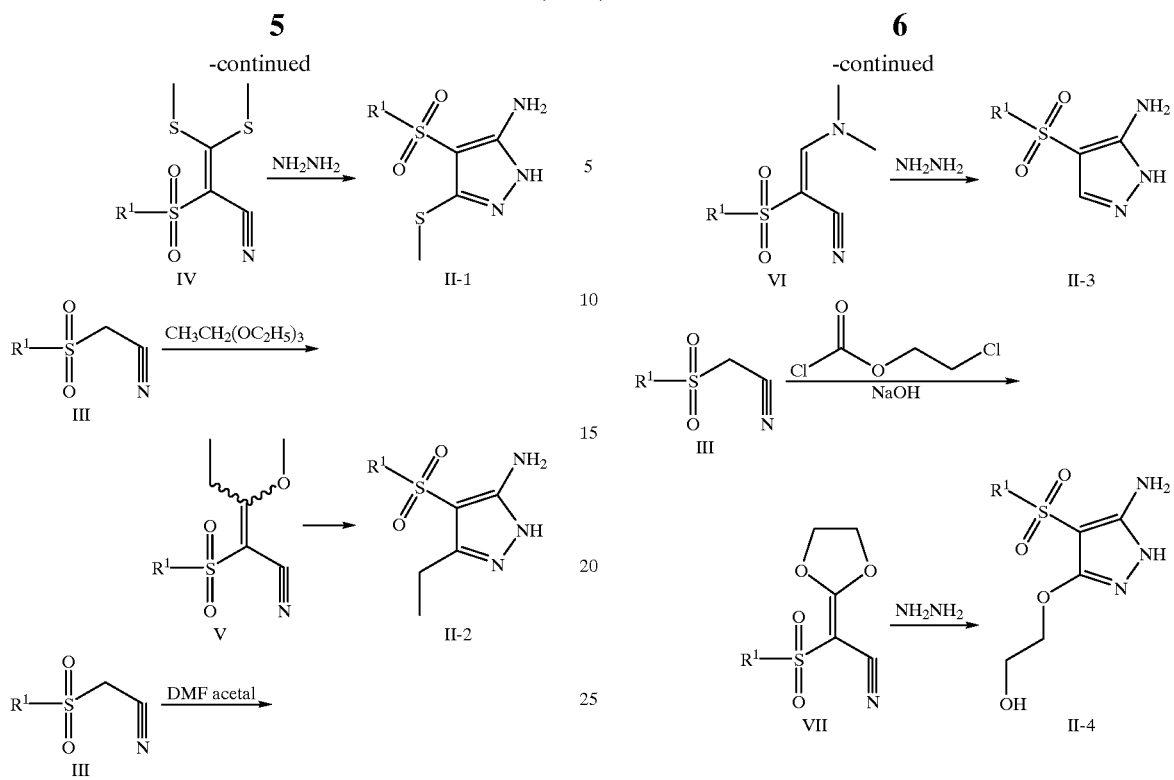
wherein $R^1$ is as represented above.
Scheme 2
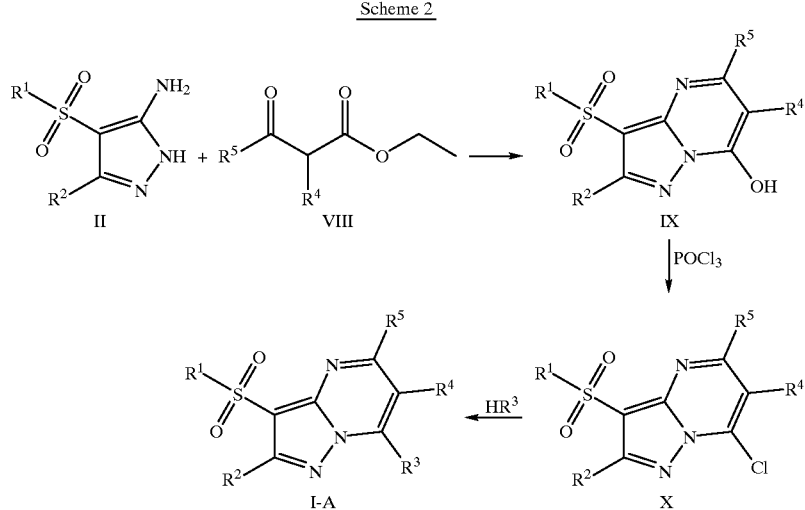
wherein $R^1$, $R^2$, $R^3$ and $R^4$ are as represented above.
Scheme 3
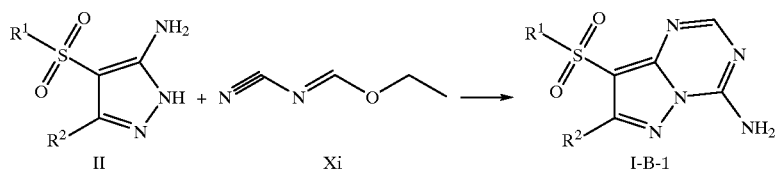

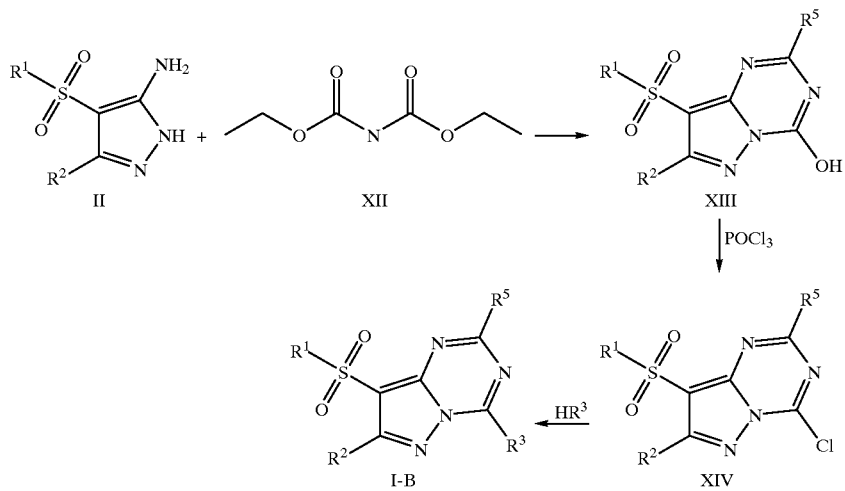

wherein $R^1, R^2, R^3$ and $R^5$ are as represented above.

The following compounds of formula I-A were manufactured according to Examples 1–123:

| Example No. | $R^1$ | $R^2$ | $R^3$ | $R^4$ | $R^5$ |
|---|---|---|---|---|---|
| 1 | Ph | $SCH_3$ | Piperazinyl | H | $CH_3$ |
| 2 | Ph | $SCH_3$ | MePiperazinyl | H | $CH_3$ |
| 3 | Ph | $SCH_3$ | $NHCH_3$ | H | $CH_3$ |
| 4 | Ph | $SCH_3$ | $NH_2$ | H | $CH_3$ |
| 5 | Ph | $SCH_3$ | $N(CH_3)_2$ | H | $CH_3$ |
| 6 | Ph | $SCH_3$ | Morpholinyl | H | $CH_3$ |
| 7 | Ph | $SCH_3$ | Imidazolyl | H | $CH_3$ |
| 8 | Ph | $SCH_3$ | Benzylpiperazinyl | H | $CH_3$ |
| 9 | Ph | $SCH_3$ | Hydroxyethylpiperazinyl | H | $CH_3$ |
| 10 | Ph | $SCH_3$ | Phenylpiperazinyl | H | $CH_3$ |
| 11 | Ph | $SCH_3$ | $(CH_3)_2N-CH_2CH_2NH$ | H | $CH_3$ |
| 12 | Ph | $SCH_3$ | 2,6-Dimethylpiperazinyl | H | $CH_3$ |
| 13 | 4-$CH_3$—Ph | $SCH_3$ | Piperazinyl | H | $CH_3$ |
| 14 | 4-$CH_3$—Ph | $SCH_3$ | MePiperazinyl | H | $CH_3$ |
| 15 | 4-$CH_3$—Ph | $SCH_3$ | $NHCH_3$ | H | $CH_3$ |
| 16 | 4-$CH_3$—Ph | $SCH_3$ | $NH_2$ | H | $CH_3$ |
| 17 | 4-$CH_3$—Ph | $SCH_3$ | $N(CH_3)_2$ | H | $CH_3$ |
| 18 | 4-$(CH_3)_2$CHPh | $SCH_3$ | Piperazinyl | H | $CH_3$ |
| 19 | 4-$(CH_3)_2$CHPh | $SCH_3$ | MePiperazinyl | H | $CH_3$ |
| 20 | 4-$(CH_3)_2$CHPh | $SCH_3$ | $NH_2$ | H | $CH_3$ |
| 21 | 4-$(CH_3)_2$CHPh | $SCH_3$ | $N(CH_3)_2$ | H | $CH_3$ |
| 22 | 4-t-Bu-Ph | $SCH_3$ | Piperazinyl | H | $CH_3$ |
| 23 | 4-t-Bu-Ph | $SCH_3$ | MePiperazinyl | H | $CH_3$ |
| 24 | 4-t-Bu-Ph | $SCH_3$ | $NH_2$ | H | $CH_3$ |
| 25 | 4-Cl-Ph | $SCH_3$ | Piperazinyl | H | $CH_3$ |
| 26 | 4-Cl-Ph | $SCH_3$ | MePiperazinyl | H | $CH_3$ |
| 27 | 4-Cl-Ph | $SCH_3$ | $NH_2$ | H | $CH_3$ |
| 28 | 4-Cl-Ph | $SCH_3$ | $N(CH_3)_2$ | H | $CH_3$ |
| 29 | 2,4-Di-Cl-Ph | $SCH_3$ | Piperazinyl | H | $CH_3$ |
| 30 | 2,4-Di-Cl-Ph | $SCH_3$ | MePiperazinyl | H | $CH_3$ |
| 31 | 2,4-Di-Cl-Ph | $SCH_3$ | $NH_2$ | H | $CH_3$ |
| 32 | 4-Br-Ph | $SCH_3$ | Piperazinyl | H | $CH_3$ |
| 33 | 4-Br-Ph | $SCH_3$ | MePiperazinyl | H | $CH_3$ |
| 34 | 4-Br-Ph | $SCH_3$ | $NH_2$ | H | $CH_3$ |
| 35 | 4-MeO-Ph | $SCH_3$ | Piperazinyl | H | $CH_3$ |
| 36 | 4-MeO-Ph | $SCH_3$ | MePiperazinyl | H | $CH_3$ |
| 37 | 4-MeO-Ph | $SCH_3$ | $NH_2$ | H | $CH_3$ |
| 38 | 2-Naphthyl | $SCH_3$ | MePiperazinyl | H | $CH_3$ |
| 39 | 2-Naphthyl | $SCH_3$ | $N(CH_3)_2$ | H | $CH_3$ |
| 40 | 2-Naphthyl | $SCH_3$ | $NH_2$ | H | $CH_3$ |
| 41 | 4-$F_3$C-O-Ph | $SCH_3$ | Piperazinyl | H | $CH_3$ |

-continued

| Example No. | R¹ | R² | R³ | R⁴ | R⁵ |
|---|---|---|---|---|---|
| 42 | 4-F₃C-O-Ph | SCH₃ | MePiperazinyl | H | CH₃ |
| 43 | 4-F-Ph | SCH₃ | Piperazinyl | H | CH₃ |
| 44 | 4-F-Ph | SCH₃ | MePiperazinyl | H | CH₃ |
| 45 | 4-F-Ph | SCH₃ | NH₂ | H | CH₃ |
| 46 | 4-I-Ph | SCH₃ | NH₂ | H | CH₃ |
| 47 | Ph | SCH₃ | Piperazinyl | CH₃ | CH₃ |
| 48 | Ph | SCH₃ | MePiperazinyl | CH₃ | CH₃ |
| 49 | Ph | SCH₃ | Piperazinyl | H | n-Propyl |
| 50 | Ph | SCH₃ | MePiperazinyl | H | n-Propyl |
| 51 | Ph | SCH₃ | Piperazinyl | H | Cyclo-propyl |
| 52 | Ph | SCH₃ | MePiperazinyl | H | Cyclo-propyl |
| 53 | Ph | SCH₃ | NH₂ | H | Cyclo-propyl |
| 54 | Ph | SCH₃ | Piperazinyl | CH₂CH₂CH₂ | |
| 55 | Ph | SCH₃ | MePiperazinyl | CH₂CH₂CH₂ | |
| 56 | Ph | SCH₃ | NH₂ | CH₂CH₂CH₂ | |
| 57 | Ph | SCH₃ | Piperazinyl | CH₂CH₂CH₂CH₂ | |
| 58 | Ph | SCH₃ | MePiperazinyl | CH₂CH₂CH₂CH₂ | |
| 59 | Ph | SCH₃ | Piperazinyl | CH₂SCH₂ | |
| 60 | Ph | SCH₃ | MePiperazinyl | CH₂SCH₂ | |
| 61 | Thiophenyl | SCH₃ | Piperazinyl | H | CH₃ |
| 62 | Thiophenyl | SCH₃ | MePiperazinyl | H | CH₃ |
| 63 | Thiophenyl | SCH₃ | NH₂ | H | CH₃ |
| 64 | Ph | SCH₃ | MePiperazinyl | H | i-Propyl |
| 65 | Ph | SCH₃ | NH₂ | H | i-Propyl |
| 66 | Ph | SCH₃ | Piperazinyl | H | t-Butyl |
| 67 | Ph | SCH₃ | Piperazinyl | H | CF₃ |
| 68 | Ph | SCH₃ | MePiperazinyl | H | CF₃ |
| 69 | Ph | Ethyl | Piperazinyl | H | CH₃ |
| 70 | Ph | Ethyl | MePiperazinyl | H | CH₃ |
| 71 | Ph | Ethyl | (CH₃)₂N—CH₂CH₂NH | H | CH₃ |
| 72 | 4-Br-Ph | Ethyl | Piperazinyl | H | CH₃ |
| 73 | 4-Br-Ph | Ethyl | MePiperazinyl | H | CH₃ |
| 74 | 4-Br-Ph | Ethyl | (CH₃)₂N—CH₂CH₂NH | H | CH₃ |
| 75 | 4-MeO-Ph | Ethyl | Piperazinyl | H | CH₃ |
| 76 | 4-MeO-Ph | Ethyl | MePiperazinyl | H | CH₃ |
| 77 | 4-MeO-Ph | Ethyl | NH₂ | H | CH₃ |
| 78 | 4-MeO-Ph | Ethyl | 2,6-Dimethylpiperazinyl | H | CH₃ |
| 79 | Ph | Ethyl | Piperazinyl | CH₂CH₂CH₂ | |
| 80 | Ph | Ethyl | MePiperazinyl | CH₂CH₂CH₂ | |
| 81 | Ph | Ethyl | NH₂ | CH₂CH₂CH₂ | |
| 82 | Ph | Ethyl | 2,6-Dimethylpiperazinyl | CH₂CH₂CH₂ | |
| 83 | Ph | H | Piperazinyl | H | CH₃ |
| 84 | Ph | H | MePiperazinyl | H | CH₃ |
| 85 | o-Tolyl | SCH₃ | Piperazinyl | H | CH₃ |
| 86 | o-Tolyl | SCH₃ | MePiperazinyl | H | CH₃ |
| 87 | o-Tolyl | SCH₃ | NH₂ | H | CH₃ |
| 88 | m-Tolyl | SCH₃ | Piperazinyl | H | CH₃ |
| 89 | m-Tolyl | SCH₃ | MePiperazinyl | H | CH₃ |
| 90 | m-Tolyl | SCH₃ | NH₂ | H | CH₃ |
| 91 | 3-Pyridyl | SCH₃ | Piperazinyl | H | CH₃ |
| 92 | 3-Pyridyl | SCH₃ | MePiperazinyl | H | CH₃ |
| 93 | 3-Pyridyl | SCH₃ | NH₂ | H | CH₃ |
| 94 | Ph | SCH₃ | MePiperazinyl | CH₂CH₂OH | CH₃ |
| 95 | Ph | OCH₂CH₂OH | MePiperazinyl | H | CH₃ |
| 96 | Ph | SCH₃ | Piperazinyl | H | CH₂CH₂O—CH₃ |
| 97 | Ph | SCH₃ | MePiperazinyl | H | CH₂CH₂O—CH₃ |
| 98 | Ph | SCH₃ | NH₂ | H | CH₂CH₂O—CH₃ |
| 99 | Ph | SCH₃ | Piperazinyl | H | CH₂OCH₃ |
| 100 | Ph | SCH₃ | MePiperazinyl | H | CH₂OCH₃ |
| 101 | Ph | SCH₃ | NH₂ | H | CH₂OCH₃ |
| 102 | Ph | SCH₃ | MePiperazinyl | H | Cl |
| 103 | Ph | SCH₃ | MePiperazinyl | H | H |
| 104 | Ph | SCH₃ | MePiperazinyl | H | OCH₂CH₂OH |
| 105 | Ph | SCH₃ | NH₂ | H | Cl |
| 106a | Ph | SCH₃ | NH₂ | H | N(CH₃)₂ |
| 106b | Ph | SCH₃ | NH₂ | H | NHCH₂CH₂—N(CH₃)₂ |
| 107 | Ph | SCH₃ | NH₂ | H | MePiperazinyl |

-continued

| Example No. | $R^1$ | $R^2$ | $R^3$ | $R^4$ | $R^5$ |
|---|---|---|---|---|---|
| 108 | Ph | Ethyl | MePiperazinyl | H | Cl |
| 109 | Ph | Ethyl | MePiperazinyl | H | H |
| 110 | Ph | Ethyl | MePiperazinyl | H | MePiperazinyl |
| 111 | Ph | Ethyl | MePiperazinyl | H | Morpholinyl |
| 112 | Ph | Ethyl | MePiperazinyl | H | $OCH_2CH_2OH$ |
| 113a | Ph | Ethyl | MePiperazinyl | H | $N(CH_3)_2$ |
| 113b | Ph | Ethyl | MePiperazinyl | H | $NHCH_2CH_2N—(CH_3)_2$ |
| 114 | Ph | Ethyl | $NH_2$ | H | Cl |
| 115 | Ph | Ethyl | $NH_2$ | H | MePiperazinyl |
| 116a | Ph | Ethyl | $NH_2$ | H | $N(CH_3)_2$ |
| 116b | Ph | Ethyl | $NH_2$ | H | $NHCH_2CH_2N—(CH_3)_2$ |
| 117 | Ph | $SCH_3$ | $NH_2$ | H | $CH_2N(CH_3)_2$ |
| 118 | Ph | $SCH_3$ | $NH_2$ | H | $CH_2NHMePip$ |
| 119 | Ph | $SCH_3$ | MePiperazinyl | H | $CH_2NHMePip$ |
| 120 | Ph | $SCH_3$ | $NH_2$ | H | $CH_2MorPh$ |
| 121 | Ph | $SCH_3$ | MePiperazinyl | H | $CH_2MorPh$ |
| 122 | Ph | $SCH_3$ | $O(CH_2)N(CH_3)_2$ | H | $CH_3$ |
| 123 | Ph | $SCH_3$ | $O(CH_2)_2$morpholinyl | H | $CH_3$ |

The following compounds of formula I-B were prepared in accordance with Synthesis Examples 122–127:

| Example No. | $R^1$ | $R^2$ | $R^3$ | $R^5$ |
|---|---|---|---|---|
| 124 | Ph | $SCH_3$ | $NH_2$ | H |
| 125 | Ph | $SCH_3$ | $NHCH_3$ | $CH_3$ |
| 126 | Ph | $SCH_3$ | $N(CH_3)_2$ | $CH_3$ |
| 127 | Ph | $SCH_3$ | $NH(CH_2)_3N—(CH_3)_2$ | $CH_3$ |
| 128 | Ph | $SCH_3$ | MePiperazinyl | $CH_3$ |
| 129 | Ph | $SCH_3$ | Benzylpiperazinyl | $CH_3$ |

As mentioned earlier, the compounds of formula I-A and I-B are novel. They have pharmacological properties and evidence a low toxicity. They have as a common feature a pronounced affinity to 5-$HT_6$ receptors and, due to their action at this receptor, are therefore suitable for the treatment or prevention of central nervous disorders such as, for example, psychoses, schizophrenia, manic depressions, neurological disorders, memory disorders, Parkinson's disease, amyotrophic lateral sclerosis, Alzheimer's disease and Huntington's chorea.

The binding of compounds of formula I-A and I-B in accordance with the invention to 5-$HT_6$ receptors was determined as follows.

Membranes obtained from HEK 1293 cells which had been transfected with 5-$HT_6$ receptors from rats were used.

The cells were purified by two-fold centrifugation (10 minutes at 3000 g) in phosphate buffer-sodium chloride solution. The cell mass was suspended in an ice-cold solution consisting of 50 mm Tris-HCl buffer, 10 mm $MgCl_2$, 0.5 mm EDTA and 0.1 mm phenylmethylsulphonyl fluoride and homogenized (Polytron homogenizer, 15 seconds at maximum speed). The homogenizate was incubated at 37° C. for 10 minutes and subsequently centrifuged (20 minutes at 20 000 g). The cell mass was again suspended in the aforementioned Tris buffer solution. The cell concentration obtained was $4 \times 10^7$ cells/ml. 1 ml aliquots of the homogenizate were frozen at −80° C.

Displacement experiments were carried out in order to determine the affinity of the test substance to the 5-$HT_6$ receptor. For the performance of the test, the homogenizate was thawed and suspended in a buffer solution (pH 7.4) consisting of 50 mm Tris-HCl buffer, 5 mm $MgCl_2$, $10^{-5}$ M pargyline and 0.1% ascorbic acid. 100 μl of membrane suspension, 50 μl of [$^3$H]-LSD (specific activity 85Ci/mMol, final concentration 1 NNI) and 50 μl of test substance solution were incubated at 37° C. for 1 hour. The respective test substance was investigated at 7 different concentrations of $10^{-10}$ M to $10^{-4}$ M. The binding reaction of the test substance was interrupted by rapid filtration through a Whatmann GF/B filter. The filters were washed with 2×2 ml of Tris-HCl buffer (50 mm pH 7.4) and the radioactivity of the filter was measured by scintillation spectroscopy in 2 ml of scintillation solution. All tests were carried out in triplicate and repeated three times. The pKi values (pKi=−$\log_{10}$ Ki) of the test substances have been determined. The Ki value is defined by the following formula $$Ki = \frac{IC_{50}}{1 + \frac{[L]}{K_D}}$$

in which the $IC_{50}$ values are those concentrations of the test compounds in NM by which 50% of the ligands bonded to the receptor are displaced. [L] is the concentration of the ligand and the $K_D$ value is the dissociation constant of the ligand.

The compounds in accordance with the invention have a selective affinity to 5-HT 6 receptors with a pKi value between 6.5 and 9.5.

The compounds of formula I-A and I-B and the pharmaceutically acceptable salts of the compounds of formula I-A and I-B can be used as medicaments, e.g. in the form of pharmaceutical preparations. The pharmaceutical preparations can be administered orally e.g. in the form of tablets, coated tablets, dragées, hard and soft gelatine capsules, solutions, emulsions or suspensions. However, the administration can also be effected rectally, e.g. in the form of suppositories, or parentally, e.g. in the form of injection solutions.

For the production of pharmaceutical preparations, the compounds of formula I-A and I-B and the pharmaceutically acceptable salts of the compounds of formula I-A and I-B can be processed with pharmaceutically inert, inorganic or organic carriers. Lactose, corn starch or derivatives thereof, talc, stearic acid or its salts and the like can be used as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active ingredient no carriers are, however, usually required in the case of soft gelatine capsules. Suitable carriers for the production of solutions and syrups are, for example, water, polyols, glycerol, vegetable oils and the like. Suitable carriers for suppositories are, for example, natural or hardened oils, waxes, fats, semi-liquid or liquid polyols and the like.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other pharmaceutically valuable substances.

Medicaments containing a compound of formula I-A or I-B or a pharmaceutically acceptable salt thereof and a therapeutically inert carrier are also an object of the present invention, as is a process for their production, which comprises bringing one or more compounds of formula I and/or pharmaceutically acceptable acid addition salts thereof and, if desired, one or more other therapeutically valuable substances together with one or more therapeutically inert carriers into a galenical administration form in a known manner.

In accordance with the invention compounds of general formula I-A and I-B as well as their pharmaceutically acceptable salts can be used in the treatment or prevention of central nervous disorders, such as depressions, psychoses, schizophrenia, neurological disorders, memory disorders, Parkinson's disease, amyotrophic lateral sclerosis, Alzheimer's disease, Huntington's chorea and for the production of corresponding medicaments. The dosage can vary within wide limits and will, of course, be fitted to the individual requirements in each particular case. In the case of oral administration the dosage lies in a range of about 0.1 mg per dose to about 1000 mg per day of a compound of general formula I-A or I-B or the corresponding amount of a pharmaceutically acceptable salt thereof, although the upper limit can also be exceeded when this is shown to be indicated.

The following Examples serve to illustrate the present invention in more detail. However, they are not intended to limit its scope in any manner.

EXAMPLE 1

3-Benzenesulphonyl-5-methyl-2-methylsulphanyl-7-piperazin-1-yl-pyrazolo-[1,5-a]pyrimidine a) A solution of 6.30 g (21 mmol) of 4-benzenesulphonyl-5-methylsulphanyl-2H-pyrazol-3-ylamine and 3.24 ml (25.8 mmol) of ethyl acetoacetate in 20 ml of acetic acid was heated at reflux for 1.5 hrs. The reaction solution was cooled to 0° C. and stirred at this temperature for 30 min. The separated crystals were filtered off under suction and dried at 50°/10 Torr. There were thus obtained 6.10 g (87%) of 3-benzenesulphonyl-5-methyl-2-methylsulphanyl-pyrazolo [1,5-a]pyrimidin-7-ol as white crystals, m.p. >220°.

b) A suspension of 3.0 g (8.94 mmol) of 3-benzenesulphonyl-5-methyl-2-methylsulphanyl-pyrazolo [1,5-a]pyrimidin-7-ol in 20 ml of POCl$_3$ was heated at reflux for 45 min. The reaction solution was cooled to RT and evaporated in a high vacuum. The residue was treated with 100 ml of ice-water and the pH value of the solution was adjusted to 8 with sat. NaHCO$_3$ solution. The aqueous phase was extracted three times with 100 ml of CH$_2$Cl$_2$, and the organic phases were dried (MgSO$_4$), filtered and evaporated. Chromatography (SiO$_2$, CH$_2$Cl$_2$/AcOEt 19:1) of the residue yielded 3.0 g (94%) of 3-benzenesulphonyl-7-chloro-5-methyl-2-methylsulphanyl-pyrazolo[1,5-a]pyrimidine as pale yellow crystals, m.p. 163–165° C.

c) 0.3 g (3.4 mmol) of piperazine in 10 ml of DMF was added to a solution of 0.6 g (1.7 mmol) of 3-benzenesulphonyl-7-chloro-5-methyl-2-methylsulphanyl-pyrazolo[1,5-a]pyrimidine in 10 ml of DMF and the mixture was stirred at 60° C. for 2 hrs. The reaction solution was cooled to RT and evaporated in a high vacuum. The residue was partitioned between 2N NaOH and CH$_2$Cl$_2$. The aqueous phase was extracted three times with CH$_2$Cl$_2$, and the combined organic phases were dried (MgSO$_4$), filtered and evaporated. Subsequent chromatography (SiO$_2$, CH$_2$Cl$_2$/MeOH 8:1) and crystallization from EtOH yielded 0.35 g (51%) of 3-benzenesulphonyl-5-methyl-2-methylsulphanyl-7-piperazin-1-yl-pyrazolo[1,5-a]pyrimidine as colorless crystals, m.p. 201–202°.

EXAMPLE 2

3-Benzenesulphonyl-5-methyl-7-(4-methyl-piperazin-1-yl)-2-methylsulphanyl-pyrazolo [1,5-a] pyrimidine 0.15 g (1.5 mmol) of 1-methyl-piperazine in 10 ml of DMF was added to a solution of 0.45 g (1.275 mmol) of 3-benzenesulphonyl-7-chloro-5-methyl-2-methylsulphanyl-pyrazolo[1,5-a]pyrimidine in 10 ml in DMF and stirred at 60° for 2 hrs. The reaction solution was cooled to RT and evaporated in a high vacuum. The residue was partitioned between 2N NaOH and CH$_2$Cl$_2$. The aqueous phase was extracted three times with CH$_2$Cl$_2$, and the combined organic phases were dried (MgSO$_4$), filtered and evaporated. Subsequent chromatography (SiO$_2$, CH$_2$Cl$_2$/MeOH 15:1) and crystallization from EtOH yielded 0.40 g (75%) of 3-benzenesulphonyl-5-methyl-7-(4-methyl-piperazine-1-yl) -2-methylsulphanyl-pyrazolo[1,5-a]pyrimidine as colorless crystals, m.p. 209–210°.

EXAMPLE 3

(3-Benzenesulphonyl-5-methyl-2-methylsulphanyl-pyrazolo[1,5-a]pyrimidin-7-yl)-methyl-amine 10 ml of a 33% solution of methylamine in EtOH was added to a solution of 0.3 g (0.85 mmol) of 3-benzenesulphonyl-7-chloro-5-methyl-2-methylsulphanyl-pyrazolo[1,5-a]pyrimidine in 5 ml of DMF and stirred at RT for 2 hrs. The reaction solution was evaporated in a high vacuum and the residue was partitioned between 2N NaOH and CH$_2$Cl$_2$. The aqueous phase was extracted three times with CH$_2$Cl$_2$, and the combined organic phases were dried (MgSO$_4$), filtered and evaporated. Subsequent chromatography (SiO$_2$,CH$_2$Cl$_2$/AcOEt 15:1) and crystallization from EtOH yielded 0.18 g (60%) of (3-benzenesulphonyl 5-methyl-2-methylsulphanyl-pyrazolo[1,5-a]pyrimidin-7-yl)-methyl-amine as colorless crystals, m.p. >230°.

EXAMPLE 4

(3-Benzenesulphonyl-5-methyl-2-methylsulphanyl-1pyrazolo[1,5-a]pyrimidin-7-yl)amine 10 ml of a 50% solution of NH$_3$ in MeOH were added to a solution of 0.40 g (1.13 mmol) of 3-benzenesulphonyl-7-chloro-5-methyl-2-methylsulphanyl-pyrazolo[1,5-a] pyrimidine in 10 ml of DMF and stirred at RT for 2 hrs. The reaction solution was evaporated in a high vacuum and the residue was partitioned between 2N NaOH and $CH_2Cl_2$. The aqueous phase was extracted three times with $CH_2Cl_2$, and the combined organic phases were dried ($MgSO_4$), filtered and evaporated. Subsequent chromatography ($SiO_2$, $CH_2Cl_2$/AcOEt 7:1) and crystallization from EtOH yielded 0.25 g (66%) of (3-benzenesulphonyl-5-methyl-2-methylsulphanyl-pyrazolo[1,5-a]pyrimidin-7-yl)amine as colorless crystals, m.p. >230°.

EXAMPLE 5

(3-Benzenesulphonyl-5-methyl-2-methylsulphanyl-pyrazolo[1,5-a]pyrimidin-7-yl)-dimethyl-amine was added to a solution of 0.30 g (0.85 mmol) 3-benzenesulphonyl-7-chloro-5-methyl-2-methylsulphanyl-pyrazolo[1,5-a]pyrimidine in 10 ml of DMF and stirred at RT for 1 hr. The reaction solution was evaporated in a high vacuum and the residue was partitioned between 2N NaOH and $CH_2Cl_2$. The aqueous phase was extracted three times with $CH_2Cl_2$, and the combined organic phases were dried ($MgSO_4$), filtered and evaporated. Subsequent chromatography ($SiO_2$, $CH_2Cl_2$/AcOEt 15:1) and crystallization from EtOH yielded 0.18 g (58%) of (3-benzenesulphonyl-5-methyl-2-methylsulphanyl-pyrazolo[1,5-a]-pyrimidin-7-yl)-dimethyl-amine as colorless crystals, m.p. >230°.

EXAMPLE 6

3-Benzenesulphonyl-5-methyl-2-methylsulphanyl-7-morpholin-4-yl-pyrazolo-[1,5-a]pyrimidine 0.20 g (2.2 mmol) of morpholine was added to a solution of 0.25 g (0.85 mmol) of 3-benzenesulphonyl-7-chloro-5-methyl-2-methylsulphanyl-pyrazolo[1,5-a]pyrimidine in 10 l of DMF and stirred at 60° for 1 hr. The reaction solution was cooled to RT and evaporated in a high vacuum. The residue was partitioned between 2N NaOH and $CH_2Cl_2$. The aqueous phase was extracted three times with $CH_2Cl_2$, and the combined organic phases were dried ($MgSO_4$), filtered and evaporated. Subsequent chromatography ($SiO_2$, $CH_2Cl_2$/MeOH 25:1) and crystallization from EtOH yielded 0.20 g (70%) of 3-benzenesulphonyl-5-methyl-2-methylsulphanyl-7-morpholin-4-yl-pyrazolo[1,5-a]pyrimidine as colorless crystals, m.p. 206–208°.

EXAMPLE 7

3-Benzenesulphonyl-7-imidazol-1-yl-5-methyl-2-methylsulphanyl-pyrazolo-[1,5-a]pyrimidine 0.08 g (1.5 mmol) of sodium methanolate was added to a suspension of 0.122 g (1.8 mmol) of imidazole in 30 ml of DMF and stirred at 60° for 15 min. Subsequently, a solution of 0.53 g (1.5 mmol) of 3-benzenesulphonyl-7-chloro-5-methyl-2-methylsulphanyl-pyrazolo[1,5-a]-pyrimidine in 10 ml of DMF was added to this suspension and stirred at 60° for 1 hr. The reaction solution was cooled to RT and evaporated in a high vacuum. The residue was partitioned between 2N NaOH and $CH_2Cl_2$. The aqueous phase was extracted three times with CH2Cl2, and the combined organic phases were dried ($MgSO_4$), filtered and evaporated. Subsequent chromatography ($SiO_2$, $CH_2Cl_2$/MeOH 15:1) and crystallization from EtOH yielded 0.30 g (51%) of 3-benzenesulphonyl-7-imidazol-1-yl-5-methyl-2-methylsulphanyl-pyrazolo[1,5-a]pyrimidine as colorless crystal, m.p. >230°.

EXAMPLE 8

3-Benzenesulphonyl-7-(4-benzyl-piperazin-1-yl)-5-methyl-2-methylsulphanyl-pyrazolo[1,5-a]pyrimidine 0.35 g (2 mmol) of N-benzyl-piperidine was added to a solution of 0.35 g (1 mmol) of 3-benzenesulphonyl-7-chloro-5-methyl-2-methylsulphanyl-pyrazolo[1,5-a]pyrimidine in 5 ml of DMF and stirred at 60° for 2 hrs. The reaction solution was cooled to RT and evaporated in a high vacuum. The residue was partitioned between 2N NaOH and $CH_2Cl_2$. The aqueous phase was extracted three times with $CH_2Cl_2$, and the combined organic phases were dried ($MgSO_4$), filtered and evaporated. Subsequent chromatography ($SiO_2$, $CH_2Cl_2$/MeOH 19:1) and crystallization from EtOH yielded 0.36 g (73%) of 3-benzenesulphonyl-7-(4-benzyl-piperazin-1-yl)-5-methyl-2-methylsulphanyl-pyrazolo[1,5-a]pyrimidine as colorless crystals m.p. 156–158°.

EXAMPLE 9

2-[4-(3-Benzenesulphonyl-5-methyl-methylsulphanyl-pyrazolo[1,5-a]pyrimidin-7-yl)-piperazin-1-yl]-ethanol 0.26 g (2 mmol) of 1(2-hydroxyethyl)-piperazine was added to a solution of 0.35 g (1 mmol) of 3-benzenesulphonyl-7-chloro-5-methyl-2-methylsulphanyl-pyrazolo[1,5 a]pyrimidine and stirred at 60° for 2 hrs. The reaction solution was cooled to RT and evaporated in a high vacuum. The residue was partitioned between 2N NaOH and $CH_2Cl_2$. The aqueous phase was extracted three times with $CH_2Cl_2$, and he combined organic phases were dried ($MgSO_4$), filtered and evaporated. Subsequent chromatography ($SiO_2$,$CH_2Cl_2$/MeOH 19:1) and crystallization from EtOH yielded 0.36 g (73%) of 2-[4(3-benzenesulphonyl-5-methyl-methylsulphanyl-pyrazolo[1,5-a]pyrimidin-7-yl)-piperazin-yl]-ethanol as colorless crystals, m.p. 189–190°.

EXAMPLE 10

3-Benzenesulphonyl-5-methyl-2-methylsulphanyl-7-(4-phenyl-piperazine-1-yl)-pyrazolo-[1,5-a]pyrimidine 0.16 g (1 mmol) of N-phenyl-piperazine was added to a solution of 0.17 g (0.5 mmol) of 3-benzenesulphonyl-7-chloro-5-methyl-2-methylsulphanyl-pyrazolo[1,5-a]pyrimidine in 3 ml of DMF and stirred at 60° for 2 hrs. The reaction solution was cooled to RT and evaporated in a high vacuum. The residue was partitioned between 2N NaOH and $CH_2Cl_2$. The aqueous phase was extracted three times with $CH_2Cl_2$, and the combined organic phases were dried ($MgSO_4$), filtered and evaporated. Subsequent chromatography ($SiO_2$, $CH_2Cl_2$/MeOH 19:1) and crystallization from EtOH yielded 0.16 g (67%) of 3-benzenesulphonyl-5-methyl-2-methylsulphanyl-7-(4-phenyl-piperazin-1-yl)-pyrazolo[1,5-a]pyrimidine as colorless crystals, m.p. >230°.

EXAMPLE 11

N-(3-Benzenesulphonyl-5-methyl-2-methylsulphanyl-pyrazolo[1,5-a]pyrimidin-7-yl )-N', N'-dimethyl-ethane-1 ,2-diamine 0.088 g (1 mmol) of 2-dimethylaminoethylamine was added to a solution of 0.17 g (0.5 mmol) of 3-benzenesulphonyl-7-chloro-5-methyl-2-methylsulphanyl-pyrazolo[1,5-a]pyrimidine in 3 ml of DMF and stirred at 60° for 2 hrs. The reaction solution was cooled to RT and evaporated in a high vacuum. The residue was partitioned between 2N NaOH and $CH_2Cl_2$. The aqueous phase was extracted three times with $CH_2Cl_2$, and the combined organic phases were dried ($MgSO_4$), filtered and evaporated. Subsequent chromatography ($SiO_2$, $CH_2Cl_2$/MeOH 19:1)

and crystallization from EtOH yielded 0.23 g (73%) of N-(3-benzenesulphonyl-5-methyl-2-methylsulphanyl-pyrazolo[1,5-a]pyrimidin-7-yl)-N',N'-dimethyl-ethane-1,2-diamine as colorless crystals, m.p. 190–191°.

EXAMPLE 12

(3R,5S)-3-Benzenesulphonyl-7-(3,5-dimethyl-piperazin-1-yl)-5-methyl-2-methylsulphanyl-pyrazolo[1,5-a]pyrimidine 0.28 g (2 mmol) of cis-2,6-dimethylpiperazine was added to a solution of 0.35 g (1 mmol) of 3-benzenesulphonyl-7-chloro-5-methyl-2-methylsulphanyl-pyrazolo[1,5-a] pyrimidine in 5 ml of DMF and stirred at 60° for 2 hrs. The reaction solution was cooled to RT and evaporated in a high vacuum. The residue was partitioned between 2N NaOH and $CH_2Cl_2$. The aqueous phase was extracted three times with $CH_2Cl_2$, and the combined organic phases were dried ($MgSO_4$), filtered and evaporated. Subsequent chromatography ($SiO_2$, $CH_2Cl_2$/MeOH 19:1) and crystallization from EtOH yielded 0.29 g (67%) of (3R,5S)-3-benzenesulphonyl-7-(3,5-dimethyl-piperazin-1-yl)-5-methyl-2-methylsulphanyl-pyrazolo[1,5-a]pyrimidine as colorless crystals, m.p. 220–221°.

EXAMPLE 13

3-Benzenesulphonyl-5-methyl-2-methylsulphanyl-7-piperazin-1-yl-pyrazolo[1,5-a]-pyrimidine a) A solution of 7.08 g (25 mmol) of 5-methylsulphanyl-4-(toluene-4-sulphonyl)-2H-pyrazol-3-ylamine and 4.0 ml (31.25 mmol) of ethyl acetoacetate in 30 l of acetic acid was heated at reflux for 1.5 hrs. The reaction solution was cooled to 0° and stirred at this temperature for 30 min. The separated crystals were filtered off under suction and dried at 50°/10 Torr. There were thus obtained 7.20 g (82%) of 5-methyl-2-methylsulphanyl-3-(toluene-4-sulphonyl)-pyrazolo[1,5-a]pyrimidin-7-ol as white crystals, m.p. >230°.

b) A suspension of 3.8 g (10.8 mmol) of 5-methyl-2-methylsulphanyl-3-(toluene-4-sulphonyl)-pyrazolo[1,5-a] pyrimidin-7-ol in 20 l of $POCl_3$ was heated at reflux for 1 hr. The reaction solution was cooled to RT and evaporated. The residue was treated with 100 ml of ice-water and the pH value of the solution was adjusted to 8 with sat. $NaHCO_3$ solution. The aqueous phase was extracted three times with $CH_2Cl_2$, and the organic phases were dried ($MgSO_4$), filtered and evaporated. Chromatography ($SiO_2$, $CH_2Cl_2$/AcOEt 25:1) of the residue yielded 3.8 g (95%) of 7-chloro-5-methyl-2-methylsulphanyl-3-(toluene-4-sulphonyl)-pyrazolo[1,5-a]pyrimidine as pale yellow crystals, m.p. 197–198°.

c) 0.3 g (3.4 mmol) of piperazine in 10 ml of DMF was added to a solution of 0.62 g (1.7 mmol) of 7-chloro-5-methyl-2-methylsulphanyl-3-(toluene-4-sulphonyl)-pyrazolo[1,5-a]pyrimidine in 10 ml of DMF and stirred at 60° for 2 hrs. The reaction solution was cooled to RT and evaporated in a high vacuum. The residue was partitioned between 2N NaOH and $CH_2Cl_2$. The aqueous phase was extracted three times with $CH_2Cl_2$, and the combined organic phases were dried ($MgSO_4$), filtered and evaporated. Subsequent chromatography ($SiO_2$, $CH_2Cl_2$/MeOH 6:1) and crystallization from EtOH yielded 0.30 g (42%) of 3-benzenesulphonyl-5-methyl-2-methylsulphanyl-7-piperazin-1-yl-pyrazolo[1,5-a]pyrimidine as colorless crystals, m.p. 137–139°.

EXAMPLE 14

5-Methyl-7-(4-methyl-piperazin-1-yl)-2-methylsulphanyl-3-(toluene-4-sulphonyl)-pyrazolo[1,5-a]pyrimidine In an analogous manner to that described in Example 2, from 7-chloro-5-methyl-2-methylsulphanyl-3-(toluene-4-sulphonyl)-pyrazolo[1,5-a]pyrimidine and 1-methyl-piperazine there was obtained 5-methyl-7-(4-methyl-piperazin-1-yl)-2-methylsulphanyl-3-(toluene-4-sulphonyl)-pyrazolo[1,5-a]pyrimidine as colorless crystals, m.p. 221–223°.

EXAMPLE 15

Methyl-[5-methyl-2-methylsulphanyl-3-(toluene-4-sulphonyl)-pyrazolo[1,5-a]pyrimidin-7-yl]-amine In an analogous manner to that described in Example 3, from 7-chloro-5-methyl-2-methylsulphanyl-3-(toluene-4-sulphonyl)-pyrazolo[1,5-a]pyrimidine and methylamine in EtOH there was obtained methyl-[5-methyl-2-methylsulphanyl-3-(toluene-4-sulphonyl)-pyrazolo[1,5-a]pyrimidin-7-yl]-amine as colorless crystals, m.p. >230°.

EXAMPLE 16

5-Methyl-2-methylsulphanyl-3-(toluene-4-sulphonyl)-pyrazolo[1,5-a]pyrimidin-7-ylamine In an analogous manner to that described in Example 4, from 7-chloro-5-methyl-2-methylsulphanyl-3-(toluene-4-sulphonyl)-pyrazolo[1,5-a]pyrimidine and $NH_3$ in MeOH there was obtained 5-methyl-2-methylsulphanyl-3-(toluene-4-sulphonyl)-pyrazolo[1,5-a]-pyrimidin-7-ylamine as colorless crystals, m.p. >230°.

EXAMPLE 17

Dimethyl-[5-methyl-2-methylsulphanyl-3-(toluene-4-sulphonyl)-pyrazolo[1,5-a]pyrimidin-7-yl]-amine In an analogous manner to that described in Example 5, from 7-chloro-5-methyl-2-methylsulphanyl-3-(toluene-4-sulphonyl)-pyrazolo[1,5-a]pyrimidine and dimethylamine in EtOH there was obtained dimethyl-[5-methyl-2-methylsulphanyl-3-(toluene-4-sulphonyl)-pyrazolo[1,5-a]pyrimidin-7-yl]-amine as colorless crystals, m.p. >230°.

EXAMPLE 18

3-(4-Isopropyl-benzenesulphonyl)-5-methyl-2-methylsulphanyl-7-piperazin-1-yl-pyrazolo[1,5-a]pyrimidine a) 1.8 g (44.6 mmol) of NaH (60% suspension in oil) were added portionwise to a solution of 5 g (22.3 mmol) of (4-isopropyl-benzenesulphonyl)-acetonitrile and 1.4 ml of $CS_2$ in 14 ml of DMSO and stirred at room temperature for 45 min. Subsequently, 2.9 ml (47 mmol) of methyl iodide were slowly added dropwise thereto and stirred at RT for 2 hrs. After the addition of 30 ml of $H_2O$ the separated crystals were filtered off under suction and crystallized from EtOH$_2$/$CH_2Cl_2$. There were thus obtained 4.9 g (67%) of 2-(4-isopropyl-benzenesulphonyl)-3,3-bis-methylsulphanyl-acrylonitrile as pale yellow crystals, m.p. 87-.

b) 0.36 ml (7.3 ml) of $NH_2NH_2$ was added to a solution of 2.0 g (6.1 mmol) of 2-(4-isopropyl-benzenesulphonyl)-3,3-bis-methylsulphanyl-acrylonitrile in 11 ml of EtOH and heated at reflux for 30 min. The pale brown solution was evaporated and chromato-graphed ($SiO_2$, $CH_2Cl_2$/MeOH 9:1). There were thus obtained 1.82 g (69%) of 4-isopropyl-benzenesulphonyl)-5-methylsulphanyl-2H-pyrazol-3-ylamine as a beige foam.

c) A solution of 1.80 g (5.8 mmol) of 4-(4-isopropyl-benzenesulphonyl)-5-methylsulphanyl)-2H-pyrazol-3- ylamine and 1.13 ml (8.8 mmol) of ethyl acetoacetate in 10 ml of acetic acid was heated at reflux for 1.5 hrs. The reaction solution was cooled to 0° and stirred at this temperature for 30 min. The separated crystals were filtered off and dried at 50°/10 Torr. There were thus obtained 1.82 g (83%) of 3-(4-isopropyl-benzenesulphonyl)-5-methyl-2-methylsulphanyl-pyrazolo[1,5-a]pyrimidin-7-ol as white crystals, m.p. >230°.

d) A suspension of 1.8 g (4.8 mmol) of of 3-(4-isopropyl-benzenesulphonyl)-5-methyl-2-methylsulphanyl-pyrazolo[1,5-a]pyrimidin-7-ol in 30 ml of POCl₃ was heated at reflux for 45 min. The reaction solution was cooled to RT and evaporated. The residue was treated with 100 ml of ice-water and the pH value of the solution was adjusted to 8 with sat. NaHCO₃ solution. The aqueous phase was extracted three times with CH₂Cl₂, and the organic phases were dried (MgSO₄), filtered and evaporated. Chromatography (SiO₂, CH₂Cl₂/AcOEt 19:1) of the residue yielded 1.78 g (93%) of 3-(4-isopropyl-benzenesulphonyl)-5-methyl-2-methylsulphanyl-pyrazolo[1,5-a]pyrimidin-7-ol as pale yellow crystals, m.p.183–184°.

e) In an analogous manner to that described in Example 1c), from 7-chloro-3-(4-isopropyl-benzenesulphonyl)-5-methyl-2-methylsulphanyl-pyrazolo[1,5-a]pyrimidine and piperazine there was obtained 3-(4-isopropyl-benzenesulphonyl)-5-methyl-2-methylsulphanyl-7-piperazin-1-yl-pyrazolo[1,5-a]pyrimidine as colorless crystals, m.p. >230°.

EXAMPLE 19

3-(4-Isopropyl-benzenesulphonyl)-5-methyl-7-(4-methyl-piperazin-1-yl)-2-methylsulphanyl-pyrazolo[1,5-a]pyrimidine In an analogous manner to that described in Example 2, from 7-chloro-3-(4-isopropyl-benzenesulphonyl)-5-methyl-2-methylsulphanyl-pyrazolo[1,5-a]pyrimidine and 1-methyl-piperazine there was obtained 3-(4-isopropyl-benzenesulphonyl)-5-methyl-7-(4-methyl-piperazin-1-yl)-2-methylsulphanyl-pyrazolo[1,5-a]pyrimidine as colorless crystals, m.p. 218–219°.

EXAMPLE 20

3-(4-Isopropyl-benzenesulphonyl)-5-methyl-7-(4-methyl-piperazin-1-yl)-2-methylsulphanyl-pyrazol[1,5-a]pyrimidine In an analogous manner to that described in Example 4, from 7-chloro-3-(4-isopropyl-benzenesulphonyl)-5-methyl-2-methylsulphanyl-pyrazolo[1,5-a]pyrimidine and NH₃ in MeOH there was obtained 3-(4-isopropyl-benzenesulphonyl)-5-methyl-7-(4-methyl-piperazin-1-yl)-2-methylsulphanyl-pyrazolo[1,5-a]pyrimidine as colorless crystals, m.p. >230°.

EXAMPLE 21

[3-(4-Isopropyl-benzenesulphonyl)-5-methyl-2-methylsulphanyl-pyrazolo[1,5-a]pyrimidin-7-yl]-dimethyl-amine In an analogous manner to that described in Example 5, from 7-chloro-3-(4-isopropyl-benzenesulphonyl)-5-methyl-2-methylsulphanyl-pyrazolo[1,5-a]pyrimidine and dimethyl-amine in EtOH there was obtained [3-(4-isopropyl-benzenesulphonyl)-5-methyl-2-methylsulphanyl-pyrazolo[1,5-a]pyrimidin-7-yl]-dimethyl-amine as colorless crystals, m.p. 222–224°.

EXAMPLE 22

3-(4-tert-Butyl-benzenesulphonyl)-5-methyl-2-methylsulphanyl-7-piperazin-1-yl-pyrazolo[1,5-a]pyrimidine a) In an analogous manner to that described in Example 18 a) to d), starting from (4-tert-butyl-benzenesulphonyl)-acetonitrile there was obtained 3-(4-tert-butyl-benzenesulphonyl)-7-chloro-5-methyl-2-methylsulphanyl-pyrazolo[1,5-a]pyrimidine as a beige foam.

b) In an analogous manner to that described in Example 1c), from 3-(4-tert-butyl-benzenesulphonyl)-7-chloro-5-methyl-2-methylsulphanyl-pyrazolo[1,5-a]pyrimidine and piperazine there was obtained 3-(4-tert-butyl-benzenesulphonyl)-5-methyl-2-methylsulphanyl-7-piperazin-1-yl-pyrazolo[1,5-a]pyrimidine as colorless crystals, m.p. 178–180°.

EXAMPLE 23

3-(4-tert-Butyl-benzenesulphonyl)-5-methyl-7-(4-methyl-piperazin-1-yl)-2-methylsulphanyl-pyrazolo[1,5-a]pyrimidine In an analogous manner to that described in Example 2, from 3-(4-tert-butyl-benzenesulphonyl)-7-chloro-5-methyl-2-methylsulphanyl-pyrazolo[1,5-a]pyrimidine and 1-methyl-piperazine there was obtained 3-(4-tert-butyl-benzenesulphonyl)-5-methyl-7-(4-methyl-piperazin-1-yl)-2-methylsulphanyl-pyrazolo[1,5-a]pyrimidine as colorless crystals, m.p. 238–239°.

EXAMPLE 24

3-(4-tert-Butyl-benzenesulphonyl)-5-methyl-2-methylsulphanyl-pyrazolo[1,5-a]pyrimidin-7-ylamine In an analogous manner to that described in Example 4, from 3-(4-tert-butyl-benzenesulphonyl)-7-chloro-5-methyl-2-methylsulphanyl-pyrazolo[1,5-a]pyrimidine and NH₃ in MeOH there was obtained 3-(4-tert-butyl-benzenesulphonyl)-5-methyl-2-methylsulphanyl-pyrazolo[1,5-a]pyrimidin-7-ylamine as colorless crystals, m.p. >230°.

EXAMPLE 25

3-(4-Chloro-benzenesulphonyl)-5-methyl-2-methylsulphanyl-7-piperazin-1-yl-pyrazolo[1,5-a]pyrimidine (a) In an analogous manner to that described in Example 18 a) to d), starting from (4-chloro-benzenesulphonyl)-acetonitrile there was obtained 7-chloro-3-(4-chloro-benzenesulphonyl)-5-methyl-2-methylsulphanyl-pyrazolo[1,5-a]pyrimidine as a colorless foam.

(b) In an analogous manner to that described in Example 1c), from 7-chloro-3-(4-chloro-benzenesulphonyl)-5-methyl-2-methylsulphanyl-pyrazolo[1,5-a]pyrimidine and piperazine there was obtained 3-(4-chloro-benzenesulphonyl)-5-methyl-2-methylsulphanyl-7-piperazin-1-yl-pyrazolo[1,5-a]pyrimidine as colorless crystals, m.p. 214–217°.

EXAMPLE 26

3-(4-Chloro-benzenesulphonyl)-5-methyl-7-(4-methyl-piperazin-1-yl)-2-methylsulphanyl-pyrazolo[1,5-a]pyrimidine In an analogous manner to that described in Example 2, from 7-chloro-3-(4-chloro-benzenesulphonyl)-5-methyl-2- methylsulphanyl-pyrazolo[1,5-a]pyrimidine and 1-methyl-piperazine there was obtained 3-(4-chloro-benzenesulphonyl)-5-methyl-7-(4-methyl-piperazin-1-yl)-2-methylsulphanyl-pyrazolo[1,5-a]pyrimidine as colorless crystals, m.p. 200–201°0.

EXAMPLE 27

3-(4-Chloro-benzenesulphonyl)-5-methyl-2-methylsulphanyl-pyrazolo[1,5-a]pyrimidin-7-ylamine In an analogous manner to that described in Example 4, from 7-chloro-3-(4-chloro-benzenesulphonyl)-5-methyl-2-methylsulphanyl-pyrazolo[1,5-a]pyrimidine and $NH_3$ in MeOH there was obtained 3-(4-chloro-benzenesulphonyl)-5-methyl-2-methylsulphanyl-pyrazolo[1,5-a]pyrimidin-7-ylamine as colorless crystals, m.p.>230°.

EXAMPLE 28

[3-(4-Chloro-benzenesulphonyl)-5-methyl-2-methylsulphanyl-pyrazolo[1,5-a]pyrimidin-7-yl]-dimethyl-amine In an analogous manner to that described in Example 5, from 7-chloro-3-(4-chloro-benzenesulphonyl)-5-methyl-2-methylsulphanyl-pyrazolo[1,5-a]pyrimidine and dimethyl-amine in EtOH there was obtained [3-(4-chloro-benzenesulphonyl)-5-methyl-2-methylsulphanyl-pyrazolo[1,5-a]pyrimidin-7-yl]-dimethyl-amine as colorless crystals, m.p. 221–223°.

EXAMPLE 29

3-(2,4-Dichloro-benzenesulphonyl)-5-methyl-2-methylsulphanyl-7-piperazin-1-yl-pyrazolo[1,5-a]pyrimidine (a) In an analogous manner to that described in Example 18 a) to d), starting from (2,4-chloro-benzenesulphonyl)-acetonitrile there was obtained 7-chloro-3-(2,4-dichloro-benzenesulphonyl)-5-methyl-2-methylsulphanyl-pyrazolo[1,5-a]pyrimidine as a colorless foam.

(b) In an analogous manner to that described in Example 1c), from 7-chloro-3-(2,4-dichloro-benzenesulphonyl)-5-methyl-2-methylsulphanyl-pyrazolo[1,5-a]pyrimidine and piperazine there was obtained 3-(2,4-dichloro-benzenesulphonyl)-5-methyl-2-methylsulphanyl-7-piperazin-1-yl-pyrazolo[1,5-a]pyrimidine as colorless crystals, m.p.>230°.

EXAMPLE 30

3-(2,4-Chloro-benzenesulphonyl)-5-methyl-7-(4-methyl-piperazin-1-yl)-2-methylsulphanyl-pyrazolo[1,5-a]pyrimidine In an analogous manner to that described in Example 2, from 7-chloro-3-(2,4-dichloro-benzenesulphonyl)-5-methyl-2-methylsulphanyl-pyrazolo[1,5-a]pyrimidine and 1-methyl-piperazine there was obtained 3-(2,4-chloro-benzenesulphonyl)-5-methyl-7-(4-methyl-piperazin-1-yl)-2-methylsulphanyl-pyrazolo[1,5-a]pyrimidine as colorless crystals, m.p.>230°.

EXAMPLE 31

3-(2,4-Chloro-benzenesulphonyl)-5-methyl-2-methylsulphanyl-pyrazolo[1,5-a]pyrimidin-7-ylamine In an analogous manner to that described in Example 4, from 7-chloro-3-(2,4-chloro-benzenesulphonyl)-5-methyl-2-methylsulphanyl-pyrazolo[1,5-a]pyrimidine and $NH_3$ in MeOH there was obtained 3-(2,4-chloro-benzenesulphonyl)-5-methyl-2-methylsulphanyl-pyrazolo[1,5-a]pyrimidin-7-ylamine as colorless crystals, m.p.>230°.

EXAMPLE 32

3-(4-Bromo-benzenesulphonyl)-5-methyl-2-methylsulphanyl-7-piperazin-1-yl-pyrazolo-[1,5-a]pyrimidine (a) In an analogous manner to that described in Example 18 a) to d), starting from (4-bromo-benzenesulphonyl)-acetonitrile there was obtained 3-(4-bromo-benzenesulphonyl)-7-chloro-5-methyl-2-methylsulphanyl-pyrazolo[1,5-a]pyrimidine as a colorless foam.

(b) In an analogous manner to that described in Example 1c), from 3-(4-bromo-benzenesulphonyl)-7-chloro-5-methyl-2-methylsulphanyl-pyrazolo[1,5-a]pyrimidine and piperazine there was obtained 3-(4-bromo-benzenesulphonyl)-5-methyl-2-methylsulphanyl-7-piperazin-1-yl-pyrazolo[1,5-a]pyrimidine as colorless crystals, m.p. 212–214°.

EXAMPLE 33

3-(4-Bromo-benzenesulphonyl)-5-methyl-7-(4-methyl-piperazin-1-yl)-2-methylsulphanyl-pyrazolo[1,5-a]pyrimidine In an analogous manner to that described in Example 2, from 3-(4-bromo-benzenesulphonyl)-7-chloro-5-methyl-2-methylsulphanyl-pyrazolo[1,5-a]pyrimidine and 1-methyl-piperazine there was obtained 3-(4-bromo-benzenesulphonyl)-5-methyl-7-(4-methyl-piperazin-1-yl)-2-methylsulphanyl-pyrazolo[1,5-a]pyrimidine as colorless crystals, m.p. 202–203°.

EXAMPLE 34

3-(4-Bromo-benzenesulphonyl)-5-methyl-2-methylsulphanyl-pyrazolo[1,5-a]pyrimidin-7-ylamine In an analogous manner to that described in Example 4, from 3-(4-bromo-benzenesulphonyl)-7-chloro-5-methyl-2-methylsulphanyl-pyrazolo[1,5-a]pyrimidine and $NH_3$ in MeOH there was obtained 3-(4-bromo-benzenesulphonyl)-5-methyl-2-methylsulphanyl-pyrazolo[1,5-a]pyrimidin-7-ylamine as colorless crystals, m.p.>230°.

EXAMPLE 35

3-(4-Methoxy-benzenesulphonyl)-5-methyl-2-methylsulphanyl-7-piperazin-1-yl-pyrazolo[1,5-a]pyrimidine (a) In an analogous manner to that described in Example 18 a) to d), starting from (4-methoxy-benzenesulphonyl)-acetonitrile there was obtained 7-chloro-3-(4-methoxy-benzenesulphonyl)-5-methyl-2-methylsulphanyl-pyrazolo[1,5-a]pyrimidine as a colorless foam.

(b) In an analogous manner to that described in Example 1c), from 7-chloro-3-(4-methoxy-benzenesulphonyl)-5-methyl-2-methylsulphanyl-pyrazolo[1,5-a]pyrimidine and piperazine there was obtained 3-(4-methoxy-benzenesulphonyl)-5-methyl-2-methylsulphanyl-7-piperazin-1-yl-pyrazolo[1,5-a]pyrimidine as colorless crystals, m.p. 176–177°.

EXAMPLE 36

3-(4-Methoxy-benzenesulphonyl)-5-methyl-7-(4-methyl-piperazin-1-yl)-2-methylsulphanyl-pyrazolo[1,5-a]pyrimidine In an analogous manner to that described in Example 2, from 7-chloro-3-(4-methoxy-benzenesulphonyl)-5-methyl-2-methylsulphanyl-pyrazolo[1,5-a]pyrimidine and 1-methyl-piperazine there was obtained 3-(4-methoxy-benzenesulphonyl)-5-methyl-7-(4-methyl-piperazin-1-yl)-2-methylsulphanyl-pyrazolo[1,5-a]pyrimidine as colorless crystals, m.p. 212–213°.

EXAMPLE 37

3-(4-Methoxy-benzenesulphonyl)-5-methyl-2-methylsulphanyl-pyrazolo[1,5-a]pyrimidin-7-ylamine In an analogous manner to that described in Example 4, from 7-chloro-3-(4-methoxy-benzenesulphonyl)-5-methyl-2-methylsulphanyl-pyrazolo[1,5-a]pyrimidine and $NH_3$ in MeOH there was obtained 3-(4-methoxy-benzenesulphonyl)-5-methyl-2-methylsulphanyl-pyrazolo[1,5-a]pyrimidin-7-ylamine as colorless crystals, m.p.>230°.

EXAMPLE 38

5-Methyl-7-(4-methyl-piperazin-1-yl)-2-methylsulphanyl-3-(naphthalene-2-sulphonyl)-pyrazolo[1,5-a]pyrimidine (a) In an analogous manner to that described in Example 18a) to d), starting from (naphthalene-2-sulphonyl)-acetonitrile there was obtained 7-chloro-5-methyl-2-methylsulphanyl-3-(naphthalene-2-sulphonyl)-pyrazolo[1,5-a]pyrimidine as a colorless foam.

(b) In an analogous manner to that described in Example 2), from 7-chloro-5-methyl-2-methylsulphanyl-3-(naphthalene-2-sulphonyl)-pyrazolo[1,5-a]pyrimidine and 1-methyl-piperazine there was obtained 5-methyl-7-(4-methyl-piperazin-1-yl)-2-methylsulphanyl-3-(naphthalene-2-sulphonyl)-pyrazolo[1,5-a]pyrimidine as colorless crystals, m.p.>230°.

EXAMPLE 39

Dimethyl-[5-methyl-2-methylsulphanyl-3-(naphthalene-2-sulphonyl)-pyrazolo[1,5-a]pyrimidin-7-yl]-amine In an analogous manner to that described in Example 6, from 7-chloro-5-methyl-2-methylsulphanyl-3-(naphthalene-2-sulphonyl)-pyrazolo[1,5-a]pyrimidine and dimethylamine in EtOH there was obtained dimethyl-[5-methyl-2-methylsulphanyl-3-(naphthalene-2-sulphonyl)-pyrazolo[1,5-a]pyrimidin-7-yl]-amine as colorless crystals, m.p.>230°.

EXAMPLE 40

5-Methyl-2-methylsulphanyl-3-(naphthalene-2-sulphonyl)-pyrazolo[1, 5-a]pyrimidine-7-ylamine In an analogous manner to that described in Example 4, from 7-chloro-5-methyl-2-methylsulphanyl-3-(naphthalene-2-sulphonyl)-pyrazolo[1,5-a]pyrimidine and $NH_3$ in MeOH there was obtained 5-methyl-2-methylsulphanyl-3-(naphthalene-2-sulphonyl)-pyrazolo[1,5-a]pyrimidine-7-ylamine as colorless crystals, m.p.>230°.

EXAMPLE 41

5-Methyl-2-methylsulphanyl-7-piperazin-1-yl-3-(4-trifluoromethoxy-benzenesulphonyl)-pyrazolo[1,5-a]pyrimidine (a) In an analogous manner to that described in Example 18 a) to d), starting from (4-trifluoromethoxy-benzenesulphonyl)-acetonitrile there was obtained 7-chloro-5-methyl-2-methylsulphanyl-3-(4-trifluoromethoxy-benzenesulphonyl)-pyrazolo[1,5-a]pyrimidine as a colorless foam.

(b) In an analogous manner to that described in Example 1c), from 7-chloro-5-methyl-2-methylsulphanyl-3-(4-trifluoromethoxybenzenesulphonyl)-pyrazolo[1,5a]pyrimidine and piperazine there was obtained 5-methyl-2-methylsulphanyl-7-piperazin-1-yl-3-(4-trifluoromethoxy-benzenesulphonyl)-pyrazolo[1,5-a]pyrimidine as colorless crystals, m.p. 203–204°.

EXAMPLE 42

5-Methyl-7-(4-methyl-piperazin-1-yl)-2-methylsulphanyl-3-(4-trifluoromethoxy-benzenesulphonyl)-pyrazolo[1,5-a]pyrimidine In an analogous manner to that described in Example 2, from 7-chloro-5-methyl-2-methylsulphanyl-3-(4-trifluoromethoxybenzenesulphonyl)-pyrazolo[1,5a]pyrimidine and 1-methyl-piperazine there was obtained 5-methyl-7-(4-methyl-piperazin-1-yl)-2-methylsulphanyl-3-(4-trifluoromethoxy-benzenesulphonyl)-pyrazolo[1,5-a]pyrimidine as colorless crystals, m.p. 213–214°.

EXAMPLE 43

3-(4-Fluoro-benzenesulphonyl)-5-methyl-2-methylsulphanyl-7-piperazin-1-yl-pyrazolo[1,5-a]pyrimidine (a) In an analogous manner to that described in Example 18a) to d), starting from (4-fluoro-benzenesulphonyl)-acetonitrile there was obtained 7-chloro-3-(4-fluoro-benzenesulphonyl)-5-methyl-2-methylsulphanyl-pyrazolo[1,5-a]pyrimidine as a colorless foam.

(b) In an analogous manner to that described in Example 1c), from 7-chloro-3-(4-fluoro-benzenesulphonyl)-5-methyl-2-methylsulphanyl-pyrazolo[1,5-a]pyrimidine and piperazine there was obtained 3-(4-fluoro-benzenesulphonyl)-5-methyl-2-methylsulphanyl-7-piperazin-1-yl-pyrazolo[1,5-a]pyrimidine as colorless crystals, m.p. 180–181°.

EXAMPLE 44

3-(4-Fluoro-benzenesulphonyl)-5-methyl-7-(4-methyl-piperazin-1-yl)-2-methylsulphanyl-pyrazolo[1,5-a]pyrimidine In an analogous manner to that described in Example 2, from 7-chloro-3-(4-fluoro-benzenesulphonyl)-5-methyl-2-methylsulphanyl-pyrazolo[1,5-a]pyrimidine and 1-methyl-piperazine there was obtained 3-(4-fluoro-benzenesulphonyl)-5-methyl-7-(4-methyl-piperazin-1-yl)-2-methylsulphanyl-pyrazolo[1,5-a]pyrimidine as colorless crystals, m.p. 197–198°.

EXAMPLE 45

3-(4-Fluoro-benzenesulphonyl)-5-methyl-2-methylsulphanyl-pyrazolo[1,5-a]pyrimidin-7-ylamine In an analogous manner to that described in Example 4, from 7-chloro-3-(4-fluoro-benzenesulphonyl)-5-methyl-2- methylsulphanyl-pyrazolo[1,5-a]pyrimidine and $NH_3$ in MeOH there was obtained 3-(4-fluoro-benzenesulphonyl)-5-methyl-2-methylsulphanyl-pyrazolo[1,5-a]pyrimidin-7-ylamine as colorless crystals, m.p.>230°.

EXAMPLE 46

3-(4-Iodo-benzenesulphonyl)-5-methyl-2-methylsulphanyl-pyrazolo[1,5-a]pyrimidine-7-ylamine (a) In an analogous manner to that described in Example 18a) to d), starting from (4-iodo-benzenesulphonyl)-acetonitrile there was obtained 7-chloro-3-(4-iodo-benzenesulphonyl)-5-methyl-2-methylsulphanyl-pyrazolo[1,5-a]pyrimidine as a colorless foam.

(b) In an analogous manner to that described in Example 4), from 7-chloro-3-(4-iodo-benzenesulphonyl)-5-methyl-2-methylsulphanyl-pyrazolo[1,5-a]pyrimidine and $NH_3$ in MeOH there was obtained 3-(4-iodo-benzenesulphonyl)-5-methyl-2-methylsulphanyl-pyrazolo[1,5-a]pyrimidine-7-ylamine as colorless crystals, m.p.>230°.

EXAMPLE 47

3-Benzenesulphonyl-5,6-dimethyl-2-methylsulphanyl-7-piperazin-1-yl-pyrazolo[1,5-a]pyrimidine (a) In an analogous manner to that described in Example 1a, b), from 4-benzenesulphonyl-5-methylsulphanyl-2H-pyrazol-3-ylamine and ethyl 2-methyl-acetoacetate there was obtained 3-benzenesulphonyl-7-chloro-5,6-dimethyl-2-methylsulphanyl-pyrazolo[1,5-a]pyrimidine as a colorless foam.

(b) In an analogous manner to that described in Example 1c), from 3-benzenesulphonyl-7-chloro-5,6-dimethyl-2-methylsulphanyl-pyrazolo[1,5-a]pyrimidine and piperazine there was obtained 3-benzenesulphonyl-5,6-dimethyl-2-methylsulphanyl-7-piperazin-1-yl-pyrazolo[1,5-a]pyrimidine as colorless crystals, m.p. 159–160°.

EXAMPLE 48

3-Benzenesulphonyl-5,6-dimethyl-7-(4-methyl-piperazin-1-yl)-2-methylsulphanyl-pyrazolo[1,5-a]pyrimidine In an analogous manner to that described in Example 1c), from 3-benzenesulphonyl-7-chloro-5,6-dimethyl-2-methylsulphanyl-pyrazolo[1,5-a]pyrimidine and 1-methyl-piperazine there was obtained 3-benzenesulphonyl-5,6-dimethyl-7-(4-methyl-piperazin-1-yl)-2-methylsulphanyl-pyrazolo[1,5-a]pyrimidine as colorless crystals, m.p. 183–185°.

EXAMPLE 49

3-Benzenesulphonyl-2-methylsulphanyl-7-piperazin-1-yl-5-propyl-pyrazolo[1,5-a]-pyrimidine (a) In an analogous manner to that described in Example 1a, b), from 4-benzenesulphonyl-5-methylsulphanyl-2H-pyrazol-3-ylamine and ethyl butyrylacetate there was obtained 3-benzenesulphonyl-7-chloro-2-methylsulphanyl-5-propyl-pyrazolo[1,5-a]pyrimidine as a colorless foam.

(b) In an analogous manner to that described in Example 1c), from 3-benzenesulphonyl-7-chloro-2-methylsulphanyl-5-propyl-pyrazolo[1,5-a]pyrimidine and piperazine there was obtained 3-benzenesulphonyl-2-methylsulphanyl-7-piperazin-1-yl-5-propyl-pyrazolo[1,5-a]pyrimidine as colorless crystals, m.p. 197–199°.

EXAMPLE 50

3-Benzenesulphonyl-7-(4-methyl-piperazin-1-yl)-2-methylsulphanyl-5-propyl-pyrazolo[1,5-a]pyrimidine In an analogous manner to that described in Example 2, from 3-benzenesulphonyl-7-chloro-2-methylsulphanyl-5-propyl-pyrazolo[1,5-a]pyrimidine and 1-methyl-piperazine there was obtained 3-benzenesulphonyl-7-(4-methyl-piperazin-1-yl)-2-methylsulphanyl-5-propyl-pyrazolo[1,5-a]pyrimidine as colorless crystals, m.p. 207–209°.

EXAMPLE 51

3-Benzenesulphonyl-5-cyclopropyl-2-methylsulphanyl-7-piperazin-1-yl-pyrazolo[1,5-a]pyrimidine a) In an analogous manner to that described in Example 1a, b), from 4-benzenesulphonyl-5-methylsulphanyl-2H-pyrazol-3-ylamine and ethyl 3-cyclopropyl-3-oxo-propionate there was obtained 3-benzenesulphonyl-7-chloro-5-cyclopropyl-2-methylsulphanyl-pyrazolo[1,5-a]pyrimidine as a colorless foam.

b) In an analogous manner to that described in Example 1c), from 3-benzenesulphonyl-7-chloro-5-cyclopropyl-2-methylsulphanyl-pyrazolo[1,5-a]pyrimidine and piperazine there was obtained 3-benzenesulphonyl-5-cyclopropyl-2-methylsulphanyl-7-piperazin-1-yl-pyrazolo[1,5-a]pyrimidine as colorless crystals, m.p. 214–215°.

EXAMPLE 52

3-Benzenesulphonyl-5-cyclopropyl-2-methylsulphanyl-7(4-methylpiperazin-1-yl)-pyrazolo[1,5-a]pyrimidine In an analogous manner to that described in Example 2, from 3-benzenesulphonyl-7-chloro-5-cyclopropyl-2-methylsulphanyl-pyrazolo[1,5-a]pyrimidine and 1-methyl-piperazine there was obtained 3-benzenesulphonyl-5-cyclopropyl-2-methylsulphanyl-7(4-methylpiperazin-1-yl)-pyrazolo[1,5-a]pyrimidine as colorless crystals, m.p. 162–164°.

EXAMPLE 53

3-Benzenesulphonyl-5-cyclopropyl-2-methylsulphanyl-pyrazolo[1,5-a]pyrimidine-7-ylamine In an analogous manner to that described in Example 4, from 3-benzenesulphonyl-7-chloro-5-cyclopropyl-2-methylsulphanyl-pyrazolo[1,5-a]pyrimidine and $NH_3$ in MeOH there was obtained 3-benzenesulphonyl-5-cyclopropyl-2-methylsulphanyl-pyrazolo[1,5-a]pyrimidine-7-ylamine as colorless crystals, m.p.>230°.

EXAMPLE 54

3-Benzenesulphonyl-2-methylsulphanyl-8-piperazin-1-yl-6,7-dihydro-5H-cyclopenta-[d]pyrazolo[1,5-a]pyrimidine a) In an analogous manner to that described in Example 1a, b), from 4-benzenesulphonyl-5-methylsulphanyl-2H- pyrazol-3-ylamine and ethyl cyclopentanone-2-carboxylate there was obtained 3-benzenesulphonyl-8-chloro-2-methylsulphanyl-6,7-dihydro-5H-cyclopenta[d]pyrazolo[1,5-a]pyrimidine as a colorless foam.

b) In an analogous manner to that described in Example 1c), from 3-benzenesulphonyl-8-chloro-2-methylsulphanyl-6,7-dihydro-5H-cyclopenta[d]pyrazolo[1,5-a]pyrimidine and piperazine there was obtained 3-benzenesulphonyl-2-methylsulphanyl-8-piperazin-1-yl-6,7-dihydro-5H-cyclopenta[d]pyrazolo[1,5-a]pyrimidine as colorless crystals, m.p. 221–222.5°.

EXAMPLE 55

3-Benzenesulphonyl-8-(4-methyl-piperazin-1-yl)-2-methylsulphanyl-6,7-dihydro-5H-cyclopenta [d] pyrazolo[1,5-a]pyrimidine In an analogous manner to that described in Example 2, from 3-benzenesulphonyl-8-chloro-2-methylsulphanyl-6,7-dihydro-5H-cyclopenta[d}pyrazolo[1,5-a]pyrimidine and 1-methyl-piperazine there was obtained 3-benzenesulphonyl-8-(4-methyl-piperazin-1-yl)-2-methylsulphanyl-6,7-dihydro-5H-cyclopenta[d]pyrazolo[1,5-a]pyrimidine as colorless crystals, m.p. 228–229.5°.

EXAMPLE 56

3-Benzenesulphonyl-2-methylsulphanyl-6,7-dihydro-5H-cyclopenta[d]pyrazolo[1,5-a]pyrimidin-8-ylamine In an analogous manner to that described in Example 4) from 3-benzenesulphonyl-8-chloro-2-methylsulphanyl-6,7-dihydro-5H-cyclopenta[d]pyrazolo[1,5-a]pyrimidine and $NH_3$ in MeOH there was obtained 3-benzenesulphonyl-2-methylsulphanyl-6,7-dihydro-5H-cyclopenta[d]pyrazolo[1,5-a]pyrimidin-8-ylamine as colorless crystals, m.p.>230°.

EXAMPLE 57

3-Benzenesulphonyl-2-methylsulphanyl-9-piperazin-1-yl-5,6,7,8-tetrahydro-pyrazolo[5,1-b]quinazoline a) In an analogous manner to that described in Example 1a, b), from 4-benzenesulphonyl-5-methylsulphanyl-2H-pyrazol-3-ylamine and ethyl cyclohexanone-2-carboxylate there was obtained 3-benzenesulphonyl-9-chloro-2-methylsulphanyl-5,6,7,8-tetrahydro-pyrazolo[5,1-b]quinazoline as a colorless foam.

b) In an analogous manner to that described in Example 1c), from 3-benzenesulphonyl-9-chloro-2-methylsulphanyl-5,6,7,8-tetrahydro-pyrazolo[5,1-b]quinazoline and piperazine there was obtained 3-benzenesulphonyl-2-methylsulphanyl-9-piperazin-1-yl-5,6,7,8-tetrahydro-pyrazolo[5,1-b]quinazoline as colorless crystals, m.p. 121–123°.

EXAMPLE 58

3-Benzenesulphonyl-9-(4-methyl-piperazin-1-yl)-2-methylsulphanyl-5,6,7,8-tetrahydro-pyrazolo[5,1-b]quinazoline In an analogous manner to that described in Example 2, from 3-benzenesulphonyl-9-chloro-2-methylsulphanyl-5,6,7,8-tetrahydro-pyrazolo[5,1-b]quinazoline and 1-methylpiperazine there was obtained 3-benzenesulphonyl-9-(4-methyl-piperazin-1-yl)-2-methylsulphanyl-5,6,7,8-tetrahydro-pyrazolo[5,1-b]quinazoline as colorless crystals, m.p. 198–200°.

EXAMPLE 59

3-Benzenesulphonyl-2-methylsulphanyl-8-piperazin-1-yl-5H,7H-pyrazolo[1,5-a]thieno[3,4-d]pyrimidine a) In an analogous manner to that described in Example 1a, b), from 4-benzenesulphonyl-5-methylsulphanyl-2H-pyrazol-3-ylamine and methyl 4-oxo-tetrahydro-thiophene-3-carboxylate there was obtained 3-benzenesulphonyl-8-chloro-2-methylsulphanyl-5H,7H-pyrazolo[1,5-a]thieno[3,4-d]pyrimidine as a colorless foam.

b) In an analogous manner to that described in Example 1c), from 3-benzenesulphonyl-8-chloro-2-methylsulphanyl-5H,7H-pyrazolo[1,5-a]thieno[3,4-d]pyrimidine and piperazine there was obtained 3-benzenesulphonyl-2-methylsulphanyl-8-piperazin-1-yl-5H,7H4-pyrazolo[1,5-a]thieno[3,4-d]pyrimidine as colorless crystals, m.p.>230°.

EXAMPLE 60

3-Benzenesulphonyl-8-(4-methyl-piperazin-1-yl)-2-methylsulphanyl-5H,7H-pyrazolo[1,5-a]thieno[3,4-d]pyrimidine In an analogous manner to that described in Example 2, from 3-benzenesulphonyl-8-chloro-2-methylsulphanyl-5H,7H-pyrazolo[1,5-a]thieno[3,4-d]pyrimidine and 1-methylpiperazine there was obtained 3-benzenesulphonyl-8-(4-methyl-piperazin-1-yl)-2-methylsulphanyl-5H,7H-pyrazolo[1,5-a]thieno[3,4-d]pyrimidine as colorless crystals, m.p.>230°.

EXAMPLE 61

5-Methyl-2-methylsulphanyl-7-piperazin-1-yl-3-(thiophene-2-sulphonyl)-pyrazolo[1,5-a]pyrimidine a) In an analogous manner to that described in Example 18a) to d), starting from thien-2-ylsulphonylacetonitrile there was obtained 7-chloro-5-methyl-2-methylsulphanyl-3-(thiophene-2-sulphonyl)-pyrazolo[1,5-a]pyrimidine as a colorless solid.

b) In an analogous manner to that described in Example 1c), from 7-chloro-5-methyl-2-methylsulphanyl-3-(thiophene-2-sulphonyl)-pyrazolo[1,5-a]pyrimidine and piperazine there was obtained 5-methyl-2-methylsulphanyl-7-piperazin-1-yl-3-(thiophen-2-sulphonyl)-pyrazolo[1,5-a]pyrimidine as colorless crystals, m.p. 229–230°.

EXAMPLE 62

5-Methyl-7-(4-methyl-piperazin-1-yl)-2-methylsulphanyl-3-(thiophene-2-sulphonyl)-pyrazolo[1,5-a]pyrimidine In an analogous manner to that described in Example 2, from 7-chloro-5-methyl-2-methylsulphanyl-3-(thiophene-2-sulphonyl)-pyrazolo[1,5-a]pyrimidine and 1-methyl-piperazine there was obtained 5-methyl-7-(4-methyl-piperazin-1-yl)-2-methylsulphanyl-3-(thiophene-2-sulphonyl)-pyrazolo[1,5-a]pyrimidine as colorless crystals, m.p.>230°.

EXAMPLE 63

5-Methyl-2-methylsulphanyl-3-(thiophene-2-sulphonyl)-pyrazolo[1,5-a]pyrimidin-7-ylamine In an analogous manner to that described in Example 4, from 7-chloro-5-methyl-2-methylsulphanyl-3-(thiophene-2- sulphonyl)-pyrazolo[1,5-a]pyrimidine and NH$_3$ in MeOH there was obtained 5-methyl-2-methylsulphanyl-3-(thiophene-2-sulphonyl)-pyrazolo[1,5-a]pyrimidin-7-ylamine as colorless crystals, m.p.>230°.

EXAMPLE 64

3-Benzenesulphonyl-5-isopropyl-7-(4-methyl-piperazin-1-yl)-2-methylsulphanyl-pyrazolo[1,5-a]pyrimidine a) In an analogous manner to that described in Example 1a, b), from 4-benzenesulphonyl-5-methylsulphanyl-2H-pyrazol-3-ylamine and ethyl isobutyrylacetate there was obtained 3-benzenesulphonyl-7-chloro-5-isopropyl-2-methylsulphanyl-pyrazolo[1,5-a]pyrimidine as a colorless foam.

b) In an analogous manner to that described in Example 2), from 3-benzenesulphonyl-7-chloro-5-isopropyl-2-methylsulphanyl-pyrazolo[1,5-a]pyrimidine and 1-methyl-piperazine there was obtained 3-benzenesulphonyl-5-isopropyl-7-(4-methyl-piperazin-1-yl)-2-methylsulphanyl-pyrazolo[1,5-a]pyrimidine as colorless crystals, m.p. 212–214°.

EXAMPLE 65

3-Benzenesulphonyl-5-isopropyl-2-methylsulphanyl-pyrazolo[1,5-a]pyrimidin-7-ylamine In an analogous manner to that described in Example 4, from 3-benzenesulphonyl-7-chloro-5-isopropyl-2-methylsulphanyl-pyrazolo[1,5-a]pyrimidine and NH$_3$ in MeOH there was obtained 3-benzenesulphonyl-5-isopropyl-2-methylsulphanyl-pyrazolo[1,5-a]pyrimidin-7-ylamine as colorless crystals, m.p. 210–211°.

EXAMPLE 66

3-Benzenesulphonyl-5-tert-butyl-2-methylsulphanyl-7-piperazin-1-yl-pyrazolo[1,5-a]pyrimidine a) 2 g (7.4 mmol) of 4-benzenesulphonyl-5-methylsulphanyl-2H-pyrazol-3-ylamine and 2.91 ml (18.3 mmol) of ethyl pivaloylacetate were added to 27 g of polyphosphoric acid and heated to 120° for 5 hrs. After cooling 100 ml of water were slowly added thereto and the mixture was extracted three times with CH$_2$Cl$_2$. The organic phase was dried (MgSO$_4$), filtered and evaporated. Chromatography (SiO$_2$, CH$_2$Cl$_2$/EtOAc) yielded 1.34 g (48%) of 3-benzenesulphonyl-5-tert-butyl-2-methylsulphanyl-pyrazolo[1,5-a]pyrimidin-7-ol as a colorless foam.

b) A suspension of 1.34 g (3.5 mmol) of 3-benzenesulphonyl-5-tert-butyl-2-methylsulphanyl-pyrazolo[1,5-a]pyrimidin-7-ol in 20 ml of POCl$_3$ was heated at reflux for 30 min. The reaction solution was cooled to RT and evaporated. The residue was treated with 100 ml of ice-water and the pH value of the solution was adjusted to 8 with sat. NaHCO$_3$ solution. The aqueous phase was extracted three times with CH$_2$Cl$_2$, and the organic phases were dried (MgSO$_4$), filtered and evaporated. Chromatography (silica gel, CH$_2$Cl$_2$/AcOEt 19:1) of the residue yielded 1.23 g (78%) g of 3-benzenesulphonyl-5-tert-butyl-7-chloro-2-methylsulphanyl-pyrazolo[1,5-a]pyrimidine as a pale yellow foam.

c) 0.67 g (7.7 mmol) of piperazine in 10 ml of DMF was added to a solution of 1.23 g (3.1 mmol) of 3-benzenesulphonyl-5-tert-butyl-7-chloro-2-methylsulphanyl-pyrazolo[1,5-a]pyrimidine in 10 ml of DMF and stirred at RT for 2 hrs. The reaction solution was evaporated and the residue was partitioned between 2N NaOH and CH$_2$Cl$_2$. The aqueous phase was extracted three times with CH$_2$Cl$_2$, and the combined organic phases were dried (MgSO$_4$), filtered and evaporated. Subsequent chromatography (SiO$_2$, CH$_2$Cl$_2$/MeOH 19:1) and crystallization from EtOH yielded 0.25 g (18%) of 3-benzenesulphonyl-5-tert-butyl-2-methylsulphanyl-7-piperazin-1-yl-pyrazolo[1,5-a]pyrimidine as colorless crystals, m.p. 236–237°.

EXAMPLE 67

3-Benzenesulphonyl-2-methylsulphanyl-7-piperazin-1-yl-5-trifluoromethyl-pyrazolo[1,5-a]pyrimidine a) In an analogous manner to that described in Example 66a), b) from 4-benzenesulphonyl-5-methylsulphanyl-2H-pyrazol-3-ylamine and ethyl 4,4,4-trifluoroacetate there was obtained 3-benzenesulphonyl-2-methylsulphanyl-5-trifluoromethyl-pyrazolo[1,5-a]pyrimidin-7-ol as a colorless foam.

b) In an analogous manner to that described in Example 1c), from 3-benzenesulphonyl-2-methylsulphanyl-5-trifluoromethyl-pyrazolo[1,5-a]pyrimidin-7-ol and piperazine there was obtained 3-benzenesulphonyl-2-methylsulphanyl-7-piperazin-1-yl-5-trifluoromethyl-pyrazolo[1,5-a]pyrimidine as colorless crystals, m.p.>230°.

EXAMPLE 68

3-Benzenesulphonyl-7-(4-methyl-piperazin-1-yl)-2-methylsulphanyl-5-trifluoromethyl-pyrazolo[1,5-a]pyrimidine In an analogous manner to that described in Example 2), from 3-benzenesulphonyl-2-methylsulphanyl-5-trifluoromethyl-pyrazolo[1,5-a]pyrimidin-7-ol and 1-methyl-piperazine there was obtained 3-benzenesulphonyl-7-(4-methyl-piperazin-1-yl)-2-methylsulphanyl-5-trifluoromethyl-pyrazolo[1,5-a]pyrimidine as colorless crystals, m.p.>230°.

EXAMPLE 69

3-Benzenesulphonyl-2-ethyl-5-methyl-7-piperazin-1-yl-pyrazolo[1,5-a]pyrimidine a) 0.2 ml of glacial acetic acid was added to a suspension of 5.0 g (27.6 mmol) of phenylsulphonylacetonitrile in 17.6 ml (88.6 mmol) of triethyl orthopropionate and subsequently heated to 140°. The EtOH formed was distilled off continuously. After 1.5 hr. the mixture was cooled the mixture was cooled to RT and evaporated to dryness in a high vacuum. There were thus obtained 7.3 g (100%) of a mixture of (E)- and (Z)-2-benzenesulphonyl-3-ethoxy-pent-2-enenitrile as a colorless oil. b) A solution of 5.2 g (19.6 mmol) of (E)- and (Z)-2-benzenesulphonyl-3-ethoxy-pent-2-enenitrile and 1.24 ml (25.5 mol) of NH$_2$NH$_2$ in 50 ml of EtOH was heated at reflux for 1 hr. The brown reaction solution was cooled to RT, evaporated and chromatographed (SiO$_2$, CH$_2$Cl$_2$/MeOH 19:1). There were thus obtained 2.9 g (59%) of 4-benzenesulphonyl-5-ethyl-2H-pyrazol-3-ylamine as a beige oil.

c) A solution of 2.9 g (11.5 mmol) of 4-benzenesulphonyl-5-ethyl-2H-pyrazol-3-ylamine and 1.8 ml (13.8 mmol) of ethyl acetoacetate in 10 ml of acetic acid was heated at reflux for 3 hrs. The reaction solution was cooled to RT and evaporated. The residue was partitioned between CH$_2$Cl$_2$ and H$_2$O and the aqueous phase was washed three times with 150 ml of CH$_2$Cl$_2$. The combined organic phases were dried (MgSO$_4$), filtered and evaporated. Crystallization from ethyl acetate yielded 2.6 g (71%) of 3-benzenesulphonyl-2-ethyl-5-methyl-pyrazolo[1,5-a]pyrimidin-7-ol as colorless crystals.

d) A suspension of 2.0 g (6.3 mmol) of 3-benzenesulphonyl-2-ethyl-5-methyl-pyrazolo-[1,5-a]pyrimidin-7-ol in 30 ml of POCl$_3$ was heated at reflux for 45 min. The reaction solution was cooled to RT and evaporated. The residue was treated with 100 ml of ice-water and the pH value of the solution was adjusted to 8 with sat. NaHCO$_3$ solution. The aqueous phase was extracted three times with 100 ml of CH$_2$Cl$_2$, and the organic phases were dried (MgSO$_4$), filtered and evaporated. Chromatography (SiO$_2$, CH$_2$Cl$_2$/MeOH 49:1) of the residue yielded 2.0 g (94%) of 3-benzenesulphonyl-7-chloro-2-ethyl-5-methyl-pyrazolo[1,5-a]pyrimidine as colorless crystals.

e) 0.64 g (7.4 mmol) of piperazine in 10 ml of DMF was added to a solution of 1.0 g (3 mmol) of 3-benzenesulphonyl-7-chloro-2-ethyl-5-methyl-pyrazolo[1,5-a]pyrimidine in 10 ml of DMF and stirred at 60° for 2 hrs. The DMF was evaporated in a high vacuum, the residue was partitioned between 2N NaOH and CH$_2$Cl$_2$. The aqueous phase was extracted three times with 50 ml of CH$_2$Cl$_2$ and the combined organic phases were dried (MgSO$_4$), filtered and evaporated. Subsequent chromatography (SiO$_2$, CH$_2$Cl$_2$/MeOH 9:1) and crystallization from EtOH yielded 0.32 g (27%) of 3-benzenesulphonyl-2-ethyl-5-methyl-7-piperazin-1-yl-pyrazolo[1,5-a]pyrimidine as colorless crystals, m.p. 150–150.8°.

EXAMPLE 70

3-Benzenesulphonyl-2-ethyl-5-methyl-7-(4-methyl-piperazin-1-yl)-pyrazolo[1,5-a]-pyrimidine In an analogous manner to that described in Example 2, from 3-benzenesulphonyl-7-chloro-2-ethyl-5-methyl-pyrazolo[1,5-a]pyrimidine and 1-methyl-piperazine there was obtained 3-benzenesulphonyl-2-ethyl-5-methyl-7-(4-methyl-piperazin-1-yl)-pyrazolo[1,5-a]pyrimidine as colorless crystals, m.p. 171–172°.

EXAMPLE 71

N-(3-Benzenesulphonyl-2-ethyl-5-methyl-pyrazolo[1,5-a]pyrimidin-7-yl)-N'N'-dimethyl-ethane-1,2-diamine In an analogous manner to that described in Example 11) from 3-benzenesulphonyl-7-chloro-2-ethyl-5-methyl-pyrazolo[1,5-a]pyrimidine and 2-dimethylaminoethylamine there was obtained N-(3-benzenesulphonyl-2-ethyl-5-methyl-pyrazolo[1,5-a]pyrimidin-7-yl)-N',N'-dimethyl-ethane-1,2-diamin

EXAMPLE 72

3-(4-Bromo-benzenesulphonyl)-2-ethyl-5-methyl-7-piperazin-1-yl-pyrazolo[1,5-a]-pyrimidine a) In an analogous manner to that described in Example 64 a) to d), from (4-bromo-benzenesulphonyl)-acetonitrile there was obtained 3-(4-bromo-benzenesulphonyl)-7-chloro-2-ethyl-5-methyl-pyrazolo[1,5-a]pyrimidine as colorless crystals.

b) In an analogous manner to that described in Example 1c), from 3-(4-bromo-benzenesulphonyl)-7-chloro-2-ethyl-5-methyl-pyrazolo[1,5-a]pyrimidine and piperazine there was obtained 3-(4-bromo-benzenesulphonyl)-2-ethyl-5-methyl-7-piperazin-1-yl-pyrazolo[1,5-a]pyrimidine as colorless crystals, m.p. 196–197°.

EXAMPLE 73

3-(4-Bromo-benzenesulphonyl)-2-ethyl-5-methyl-7-piperazin-1-yl-pyrazolo-[1,1-a]pyrimidine In an analogous manner to that described in Example 2, from 3-(4-bromo-benzenesulphonyl)-7-chloro-2-ethyl-5-methyl-pyrazolo[1,5-a]pyrimidine and 1-methyl-piperazine there was obtained 3-(4-bromo-benzenesulphonyl)-2-ethyl-5-methyl-7-piperazin-1-yl-pyrazolo[1,5-a]pyrimidine as colorless crystals, m.p. 215–216°.

EXAMPLE 74

N-[3-(4-Bromo-benzenesulphonyl)-2-ethyl-5-methyl-pyrazolo[1,5-a]pyrimidin-7-yl]-N',N'-dimethyl-ethane-1,2-diamine In an analogous manner to that described in Example 11, from 3-(4-bromo-benzenesulphonyl)-7-chloro-2-ethyl-5-methyl-pyrazolo[1,5-a]pyrimidine and 2-dimethylamino-ethylamine there was obtained N-[3-(4-bromo-benzenesulphonyl)-2-ethyl-5-methyl-pyrazolo[1,5-a]pyrimidin-7-yl]-N',N'-dimethyl-ethane-1,2-diamine as colorless crystals, m.p. 210–211°.

EXAMPLE 75

2-Ethyl-3-(4-methoxy-benzenesulphonyl)-5-methyl-7-piperazin-1-yl-pyrazolo[1,5-a]-pyrimidine a) In an analogous manner to that described in Example 69a) to d), from (4-methoxy-benzenesulphonyl)-acetonitrile there was obtained 7-chloro-2-ethyl-3-(4-methoxy-benzenesulphonyl)-5-methyl-pyrazolo[1,5-a]pyrimidine as colorless crystals.

b) In an analogous manner to that described in Example 1c), from 7-chloro-2-ethyl-3-(4-methoxy-benzenesulphonyl)-5-methyl-pyrazolo[1,5-a]pyrimidine and piperazine there was obtained 2-ethyl-3-(4-methoxy-benzenesulphonyl)-5-methyl-7-piperazin-1-yl-pyrazolo[1,5-a]pyrimidine as colorless crystals, m.p. 196–197°.

EXAMPLE 76

2-Ethyl-3-(4-methoxy-benzenesulphonyl)-5-methyl-7-(4-methyl-piperazin-1-yl)-pyrazolo[1,5-a]pyrimidine In an analogous manner to that described in Example 2, from 7-chloro-2-ethyl-3-(4-methoxy-benzenesulphonyl)-5-methyl-pyrazolo[1,5-a]pyrimidine and 1-methyl-piperazine there was obtained 2-ethyl-3-(4-methoxy-benzenesulphonyl)-5-methyl-7-(4-methyl-piperazin-1-yl)-pyrazolo[1,5-a]pyrimidine as colorless crystals, m.p. 178–188°.

EXAMPLE 77

2-Ethyl-3-(4-methoxy-benzenesulphonyl)-5-methyl-pyrazolo[1,5-a]pyrimidin-7-ylamine In an analogous manner to that described in Example 4, from 7-chloro-2-ethyl-3-(4-methoxy-benzenesulphonyl)-5-methyl-pyrazolo[1,5-a]pyrimidine and NH$_3$ in MeOH there was obtained 2-ethyl-3-(4-methoxy-benzenesulphonyl)-5- methyl-pyrazolo[1,5-a]pyrimidin-7-ylamine as colorless crystals, m.p. 186–188°.

EXAMPLE 78

(3R,5S)-7-(3,5-Dimethyl-piperazin-1-yl)-2-ethyl-3-(4-methoxy-benzenesulphonyl)-5-methyl-pyrazolo[1,5-a]pyrimidine In an analogous manner to that described in Example 12, from 7-chloro-2-ethyl-3-(4-methoxy-benzenesulphonyl)-5-methyl-pyrazolo[1,5-a]pyrimidine and cis-2,6-dimethyl-piperazine there was obtained (3R,5S)-7-(3,5-dimethyl-piperazin-1-yl)-2-ethyl-3-(4-methoxy-benzenesulphonyl)-5-methyl-pyrazolo[1,5-a]pyrimidine as colorless crystals, m.p. 151–152°.

EXAMPLE 79

3-Benzenesulphonyl-2-ethyl-8-piperazin-1-yl-6,7-dihydro-5H-cyclopenta[d]pyrazolo[1,5-a]pyrimidine a) In an analogous manner to that described in Example 69c) d), from 4-benzenesulphonyl-5-ethyl-2H-pyrazol-3-ylamine and ethyl cyclopentanone-2-carboxylate there was obtained 3-benzenesulphonyl-8-chloro-2-ethyl-6,7-dihydro-5H-cyclopenta[d]pyrazolo[1,5-a]pyrimidine as a colorless foam.

b) In an analogous manner to that described in Example 1c), from 3-benzenesulphonyl-8-chloro-2-ethyl-6,7-dihydro-5H-cyclopenta[d]pyrazolo[1,5-a]pyrimidine and piperazine there was obtained 3-benzenesulphonyl-2-ethyl-8-piperazin-1-yl-6,7-dihydro-5H-cyclopenta[d]pyrazolo[1,5-a]pyrimidine as colorless crystals, m.p. 200–201°.

EXAMPLE 80

3-Benzenesulphonyl-2-ethyl-8-(4-methyl-piperazin-1-yl)-6,7-dihydro-5H-cyclopenta[d]-pyrazolo[1,5-a]pyrimidine In an analogous manner to that described in Example 2, from 3-benzenesulphonyl-8-chloro-2-ethyl-6,7-dihydro-5H-cyclopenta[d]pyrazolo[1,5-a]pyrimidine and 1-methyl-piperazine there was obtained 3-benzenesulphonyl-2-ethyl-8-(4-methyl-piperazin-1-yl)-6,7-dihydro-5H-cyclopenta[d]pyrazolo[1,5-a]pyrimidine as colorless crystals, m.p. 235–236°.

EXAMPLE 81

3-Benzenesulphonyl-2-ethyl-6,7-dihydro-5H-cyclopenta[d]pyrazolo[1,5-a]pyrimidin-8-ylamine In an analogous manner to that described in Example 4, from 3-benzenesulphonyl-8-chloro-2-ethyl-6,7-dihydro-5H-cyclopenta[d]pyrazolo[1,5-a]pyrimidine and $NH_3$ in MeOH there was obtained 3-benzenesulphonyl-2-ethyl-6,7-dihydro-5H-cyclopenta[d]pyrazolo[1,5-a]pyrimidin-8-ylamine as colorless crystals, m.p.>230°.

EXAMPLE 82

(3R,5S)-3-Benzenesulphonyl-8-(3,5-dimethyl-piperazin-1-yl)-2-ethyl-6,7-dihydro-5H-cyclopenta[d]pyrazolo[1,5-a]pyrimidine In an analogous manner to that described in Example 12, from 3-benzenesulphonyl-8-chloro-2-ethyl-6,7-dihydro-5H-cyclopenta[d]pyrazolo[1,5-a]pyrimidine and cis-2,6-dimethylpiperazine there was obtained (3R,5S)-3-benzenesulphonyl-8-(3,5-dimethyl-piperazin-1-yl)-2-ethyl-6,7-dihydro-5H-cyclopenta[d]pyrazolo[1,5-a]pyrimidine as colorless crystals, m.p. 220–221°.

EXAMPLE 83

3-Benzenesulphonyl-5-methyl-7-piperazin-1-yl-pyrazolo[1,5-a]pyrimidine a) 6.88 ml of N,N-dimethylformamide dimethyl acetal were added to a suspension of 7.0 g (38.6 mmol) of phenylsulphonylacetonitrile in 30 ml of hexane while cooling with ice and subsequently stirred at RT for 12 hrs. The separated crystals were filtered off and there were thus obtained 9.08 g (99%) of 2-benzenesulphonyl-3-dimethylamino-acrylonitrile as beige crystals, m.p. 108–110°.

b) 2.05 ml (40.9 mmol) of $NH_2NH_2$ were added to a solution of 9.08 g (38.3 mmol) of 2-benzenesulphonyl-3-dimethylamino-acrylonitrile in 60 ml of EtOH and stirred at 40° for 5 hrs. The reaction solution was evaporated and the residue was partitioned between $H_2O$ and $CH_2Cl_2$. The aqueous phase was washed three times with $CH_2Cl_2$, and the combined organic phases were dried ($MgSO_4$), filtered and evaporated. Chromatography ($SiO_2$, $CH_2Cl_2$/MeOH 10:1) yielded 2.5 g (30%) of 4-benzenesulphonyl-1H-pyrazol-3-ylamine as a beige powder, m.p. 159–161°.

c) A solution of 1.0 g (4.47 mmol) of 4-benzenesulphonyl-1H-pyrazol-3-ylamine and 0.6 ml (5.37 mmol) of ethyl acetoacetate in 8 ml of acetic acid was heated at reflux for 1.5 hrs. The reaction solution was cooled to RT and evaporated. The residue was partitioned between $CH_2Cl_2$ and $H_2O$ and the aqueous phase was washed three times with 150 ml of $CH_2Cl_2$. The combined organic phases were dried ($MgSO_4$), filtered and evaporated. Chromatography ($SiO_2$, $CH_2Cl_2$/MeOH 20:1) yielded 0.91 g (70%) of 3-benzenesulphonyl-5-methyl-pyrazolo[1,5-a]pyrimidine as beige crystals.

d) A suspension of 0.91 g (3.14 mmol) of 3-benzenesulphonyl-5-methyl-pyrazolo[1,5-a]pyrimidine in 15 ml of $POCl_3$ was heated at reflux for 1 hr. The reaction solution was cooled to RT and evaporated. The residue was treated with 30 ml of ice-water and the pH value of the solution was adjusted to 8 with sat. $NaHCO_3$ solution. The aqueous phase was extracted three times with 20 ml of $CH_2Cl_2$, and the organic phases were dried ($MgSO_4$), filtered and evaporated. Chromatography ($SiO_2$, $CH_2Cl_2$/AcOEt 19:1) of the residue yielded 0.84 g (87%) of 3-benzenesulphonyl-7-chloro-5-methyl-pyrazolo[1,5-a]pyrimidine as a beige solid.

e) In an analogous manner to that described in Example 1c), from 3-benzenesulphonyl-7-chloro-5-methyl-pyrazolo[1,5-a]pyrimidine and piperazine there was obtained 3-benzenesulphonyl-5-methyl-7-piperazin-1-yl-pyrazolo[1,5-a]pyrimidine as colorless crystals, m.p. 180–1810.

EXAMPLE 84

3-Benzenesulphonyl-5-methyl-7-(4-methyl-piperazin-1-yl)-pyrazolo[1,5-a]pyrimidine In an analogous manner to that described in Example 2, from 3-benzenesulphonyl-7-chloro-5-methyl-pyrazolo[1,5-a]pyrimidine and 1-methyl-piperazine there was obtained 3-benzenesulphonyl-5-methyl-7-(4-methyl-piperazin-1-yl)-pyrazolo[1,5-a]pyrimidine as colorless crystals, m.p.>230.

EXAMPLE 85

5-Methyl-2-methylsulphanyl-7-piperazin-1-yl-3-(toluene-2-sulphonyl)-pyrazolo-[1,5-a]pyrimidine In an analogous manner to that described in Example 18 a) to d), starting from (toluene-2-sulphonyl)-acetonitrile there was obtained 7-chloro-5-methyl-2-methylsulphanyl-3-(toluene-2-sulphonyl)-pyrazolo[1,5-a]pyrimidine as a colorless foam.

b) In an analogous manner to that described in Example 1c), from 7-chloro-5-methyl-2-methylsulphanyl-3-(toluene-2-sulphonyl)-pyrazolo[1,5-a]pyrimidine and piperazine there was obtained 5-methyl-2-methylsulphanyl-7-piperazin-1-yl-3-(toluene-2-sulphonyl)-pyrazolo[1,5-a]pyrimidine as colorless crystals, m.p. 215–215.5°

The (toluene-2-sulphonyl)-acetonitrile used was prepared as follows:

2.2 ml (34.5 mmol) of chloroacetonitrile were added to a suspension of 4.5 g (28.8 mmol) of toluene-2-sulphinic acid sodium salt in 100 ml of DMF and stirred at 1000 for 1 hr. The reaction solution was evaporated and the residue was partitioned between $H_2O$ and $CH_2Cl_2$. The aqueous phase was washed three times with $CH_2Cl_2$. The combined organic phases were washed once with $H_2O$, dried ($MgSO_4$). filtered and evaporated. Chromatography ($SiO_2$, $CH_2Cl_2$) yielded 2.9 g (50%) of (toluene-2-sulphonyl)-acetonitrile as a colorless oil.

EXAMPLE 86

5-Methyl-7-(4-methyl-piperazin-1-yl)-2-methylsulphanyl-3-(toluene-2-sulphonyl)-pyrazolo[1,5-a]pyrimidine In an analogous manner to that described in Example 2), from 7-chloro-5-methyl-2-methylsulphanyl-3-(toluene-2-sulphonyl)-pyrazolo[1,5-a]pyrimidine and 1-methyl-piperazine there was obtained 5-methyl-7-(4-methyl-piperazin-1-yl)-2-methylsulphanyl-3-(toluene-2-sulphonyl)-pyrazolo[1,5-a]pyrimidine as colorless crystals, m.p. 199–200°.

EXAMPLE 87

5-Methyl-2-methylsulphanyl-3-(toluene-2-sulphonyl)-pyrazolo[1,5-a]pyrimidin-7-ylamine In an analogous manner to that described in Example 4), from 7-chloro-5-methyl-2-methylsulphanyl-3-(toluene-2-sulphonyl)-pyrazolo[1,5-a]pyrimidine and $NH_3$ in MeOH there was obtained 5-methyl-2-methylsulphanyl-3-(toluene-2-sulphonyl)-pyrazolo[1,5-a]-pyrimidin-7-ylamine as colorless crystals, m.p.>250°.

EXAMPLE 88

5-Methyl-2-methylsulphanyl-7-piperazin-1-yl-3-(toluene-2-sulphonyl)-pyrazolo[1,5-a]-pyrimidine a) In an analogous manner to that described in Example 18 a) to d), starting from (toluene-3-sulphonyl)-acetonitrile there was obtained 7-chloro-5-methyl-2-methylsulphanyl-3-(toluene-3-sulphonyl)-pyrazolo[1,5-a]pyrimidine as a colorless foam.

b) In an analogous manner to that described in Example 1c), from 7-chloro-5-methyl-2-methylsulphanyl-3-(toluene-2-sulphonyl)-pyrazolo[1,5-a]pyrimidine and piperazine there was obtained 5-methyl-2-methylsulphanyl-7-piperazin-1-yl-3-(toluene-2-sulphonyl)-pyrazolo[1,5-a]pyrimidine as colorless crystals, m.p. 165–165.5°.

The (toluene-3-sulphonyl)-acetonitrile used was prepared as follows:

2.65 ml (42 mmol) of chloroacetonitrile were added to a suspension of 7.5 g (42 mmol) of toluene-3-sulphinic acid sodium salt in 80 ml of DMF and stirred at 100° for 1 hr. The reaction solution was evaporated, the residue was partitioned between $H_2O$ and $CH_2Cl_2$. The aqueous phase was washed three times with $CH_2Cl_2$. The combined organic phases were washed once with $H_2O$, dried ($MgSO_4$). filtered and evaporated. Chromatography ($SiO_2$, $CH_2Cl_2$) yielded 2.06 g (25%) of (toluene-3-sulphonyl)-acetonitrile as a colorless oil.

EXAMPLE 89

5-Methyl-7-(4-methyl-piperazin-1-yl)-2-methylsulphanyl-3-(toluene-3-sulphonyl)-pyrazolo[1,5-a]pyrimidine In an analogous manner to that described in Example 2), from 7-chloro-5-methyl-2-methylsulphanyl-3-(toluene-3-sulphonyl)-pyrazolo[1,5-a]pyrimidine and 1-methyl-piperazine there was obtained 5-methyl-7-(4-methyl-piperazin-1-yl)-2-methylsulphanyl-3-(toluene-3-sulphonyl)-pyrazolo[1,5-a]pyrimidine as colorless crystals, m.p. 183–184°.

EXAMPLE 90

5-Methyl-2-methylsulphanyl-3-(toluene-3-sulphonyl)-pyrazolo[1,5-a]pyrimidin-7-ylamine In an analogous manner to that described in Example 4)) from 7-chloro-5-methyl-2-methylsulphanyl-3-(toluene-3-sulphonyl)-pyrazolo[1,5-a]pyrimidine and $NH_3$ in MeOH there was obtained 5-methyl-2-methylsulphanyl-3-(toluene-3-sulphonyl)-pyrazolo[1,5-a]pyrimidine-7-ylamine as colorless crystals, m.p.>2500.

EXAMPLE 91

5-Methyl-2-methylsulphanyl-7-piperazin-1-yl-3-(pyridine-3-sulphonyl)-pyrazolo[1,5-a]pyrimidine a) In an analogous manner to that described in Example 18 a) to d), starting from (pyridine-3-sulphonyl)-acetonitrile there was obtained 7-chloro-5-methyl-2-methylsulphanyl-3-(pyridine-3-sulphonyl)-pyrazolo[1,5-a]pyrimidine as a colorless foam.

b) In an analogous manner to that described in Example 1c), from 7-chloro-5-methyl-2-methylsulphanyl-3-(pyridine-3-sulphonyl)-pyrazolo[1,5-a]pyrimidine and piperazine there was obtained 5-methyl-2-methylsulphanyl-7-piperazin-1-yl-3-(pyridine-3-sulphonyl)-pyrazolo[1,5-a]pyrimidine as colorless crystals, m.p. 222–223°.

The (pyridine-3-sulphonyl)-acetonitrile used was prepared as follows:

2.1 ml (33.4 mmol) of chloroacetonitrile were added to a solution of 4.6 g (42 mmol) of pyridine-3-sulphinic acid sodium salt in 50 ml of DMF and stirred at 90° for 1 hr. The reaction solution was evaporated, the residue was partitioned between $H_2O$ and $CH_2Cl_2$. The aqueous phase was washed three times with $CH_2Cl_2$. The combined organic phases were washed once with $H_2O$, dried ($MgSO_4$) filtered and evaporated. Chromatography ($SiO_2$, AcOEt/hexane 2:1) yielded 4.1 g (80%) of (pyridine-3-sulphonyl)-acetonitrile as a beige solid.

EXAMPLE 92

5-Methyl-7-(4-methyl-piperazin-1-yl)-2-methylsulphanyl-3-(pyridine-3-sulphonyl)-pyrazolo[1 ,5-a]pyrimidine In an analogous manner to that described in Example 2), from 7-chloro-5-methyl-2-methylsulphanyl-3-(pyridine-3- sulphonyl)-pyrazolo[1,5-a] pyrimidine and 1-methyl-pipazine there was obtained 5-methyl-7-(4-methyl-piperazin-1-yl)-2-methylsulphanyl-3-(pyridine-3-sulphonyl)-pyrazolo[1,5-a]pyrimidine as colorless crystals, m.p. 188.4–189°.

EXAMPLE 93

5-Methyl-2-methylsulphanyl-3-(pyridine-3-sulphonyl)-pyrazolo[1,5-a]pyrimidin-7-ylamine In an analogous manner to that described in Example 4), from 7-chloro-5-methyl-2-methylsulphanyl-3-(pyridine-3-sulphonyl)-pyrazolo[1,5-a]pyrimidine and $NH_3$ in MeOH there was obtained 5-methyl-2-methylsulphanyl-3-(pyridine-3-sulphonyl) -pyrazolo[1,5-a]pyrimidin-7-ylamine as colorless crystals, m.p. 226.8 –227.5°.

EXAMPLE 94

2-[3-Benzenesulphonyl-5-methyl-7-(4-methyl-piperazin-1-yl)-2-methylsulphanyl-pyrazolo[1,5-a]pyrimidin-6-yl]-ethanol a) A solution of 2.69 g (10 mmol) of 4-benzenesulphonyl-5-methylsulphanyl-2H-pyrazol-3-ylamine and 1.28 g (10 mmol) of 2-acetyl-butyrolactone in 10 ml of acetic acid was heated at reflux for 1.5 hrs. After cooling to RT the mixture was treated with 50 ml of $H_2O$ and extracted three times with $CH_2Cl_2$. The organic phases were dried ($MgSO_4$), filtered and evaporated. Chromatography ($SiO_2$, $CH_2Cl_2$/MeOH 20:1) of the residue yielded 1.5 g (36%) of ethyl 2-(3-benzenesulphonyl-7-hydroxy-5-methyl-2-methylsulphanyl-pyrazolo[1,5-a]pyrimidin-6-yl)-acetate as a colorless foam.

b) A suspension of 1.5 g (3.56 mmol) of ethyl 2-(3-benzenesulphonyl-7-hydroxy-5-methyl -2-methylsulphanyl-pyrazolo[1,5-a]pyrimidin-6-yl)-acetate in 30 ml of $POCl_3$ was heated at reflux for 4 hrs. The reaction solution was cooled to RT and evaporated. The residue was treated with 100 ml of ice-water and the pH value of the solution was adjusted to 8 with sat. $NaHCO_3$ solution. The aqueous phase was extracted three times with 70 ml of $CH_2Cl_2$, and the organic phases were dried ($MgSO_4$), filtered and evaporated.Chroma-tography ($SiO_2$, $CH_2Cl_2$ 20:1) of the residue yielded 1.0 g (94%) of ethyl 2-(3-benzenesulphonyl-7-chloro-5-methyl-2-methylsulphanyl-pyrazolo[1,5-a]pyrimidin-6-yl)-aceate as a pale yellow solid.

c) 0.1 g (1 mmol) of 1-methyl-piperazine in 5 ml of DMF was added to a solution of 0.35 g (0.8 mmol) of ethyl 2-(3-benzenesulphonyl-7-chloro-5-methyl-2-methylsulphanylpyrazolo[1,5-a]pyrimidin-6-yl)-acetate in 15 ml of DMF and stirred at 60° for 2 hrs. The DMF was evaporated in a high vacuum, the residue was partitioned between 2N NaOH and $CH_2Cl_2$, the aqueous phase was extracted three times with $CH_2Cl_2$. The combined organic phases were dried ($MgSO_4$), filtered and evaporated. Subsequent chromatography ($SiO_2$, $CH_2Cl_2$/MeOH 10:1) yielded 0.34 g of a yellow foam, which was dissolved in a mixture of 50 ml of tetrahydrofuran/dioxan/$H_2O$ 1:1:1. After the addition of 4 ml of 2N NaOH the mixture was stirred at 45° for 12 hrs., treated with 100 ml of $H_2O$ and extracted three times with 60 ml of $CH_2Cl_2$. The combined organic phases were dried ($MgSO_4$), filtered and evaporated. Chromatography ($SiO_2$, $CH_2Cl_2$/MeOH 8:1) yielded 0.18 mg (48%) of 2-[3-benzenesulphonyl-5-methyl-7-(4-methyl-piperazin-1-yl)-2-methylsulphanyl-pyrazolo[1,5-a]pyrimidin-6-yl]-ethanol as a colorless foam.

EXAMPLE 95

2-[3-Benzenesulphonyl-5-methyl-7-(4-methyl-piperazin-1-yl)-pyrazolo[1,5-a]pyrimidin-2-yloxy]-ethanol a) 0.88 g (22 mmol) of powdered NaOH was added to a solution of 2 g (11 mmol) of phenysulphonylacetonitrile in 20 ml of acetonitrile and stirred at RT for 2 hrs. Subsequently, a solution of 1.14 ml (11 mmol) of 2-chloroethyl chloroformate in 4 ml of acetonitrile was added dropwise thereto at 5° and the mixture was heated at reflux for 1 hr. After cooling to RT the precipitate was filtered off and the filtrate was evaporated. The thus-obtained brown oil was taken up in 50 ml of EtOH and treated with 0.54 ml (11 mmol) of $NH_2NH_2$ and heated at reflux for 1 hr. After evaporation of the reaction solution and subsequent chromatography ($SiO_2$, $CH_2Cl_2$/MeOH/$NH_4OH$ 110:10:1) there were obtained 1.4 g (45%) of 2-(5-amino-4-benzenesulphonyl-1H-pyrazol-3-yloxy)-ethanol as a colorless solid.

b) 0.75 ml of ethyl acetoacetate was added to a solution of 1.14 g (4.9 mol) of 2-(5-amino-4-benzenesulphonyl-1H-pyrazol-3-yloxy)-ethanol in 10 ml of acetic acid and heated at reflux for 3 hrs. After cooling to RT the mixture was treated with 50 ml of $H_2O$ and extracted three times with $CH_2Cl_2$. The organic phases were dried ($MgSO_4$), filtered and evaporated. Chromatography ($SiO_2$, $CH_2Cl_2$/MeOH 19:1) of the residue yielded 0.8 g (42%) of ethyl 2-(3-benzenesulphonyl-7-hydroxy-5-methyl-pyrazolo[1,5-a]pyrimidin-2-yloxy)-acetate as a colorless oil.

c) A suspension of 0.8 g (2 mmol) of ethyl 2-(3-benzenesulphonyl-7-hydroxy-5-methylpyrazolo[1,5-a]pyrimidin-2-yloxy)-acetate in 20 ml of $POCl_3$ was heated at reflux for 4 hrs. The reaction solution was cooled to RT and evaporated. The residue was treated with 80 ml of ice-water and the pH value of the solution was adjusted to 8 with sat. $NaHCO_3$ solution. The aqueous phase was extracted three times with 70 ml of $CH_2Cl_2$, and the organic phases were dried ($MgSO_4$), filtered and evaporated. Chromatography ($SiO_2$, $CH_2Cl_2$/MeOH 40:1) of the residue yielded 0.56 g (68%) of ethyl 2-[3-benzenesulphonyl-5-methyl-7-(4-methyl-pipazin-1-yl)-pyrazolo[1,5-a]pyrimidin-2-yloxy]-acetate as a colorless solid.

d) 0.38 ml (3.4 mmol) of 1-methyl-piperazine in 5ml of DMF was added to a solution of 0.56 g (1.4 mmol) of ethyl 2-[3-benzenesulphonyl-5-methyl-7-(4-methyl-piperazin-1-yl)-pyrazolo[1,5-alpyrimidin-2-yloxy]-acetate in 10 ml of DMF and stirred at RT for 1.5 hrs. The DMF was evaporated in a high vacuum,and the residue was partitioned between 2N NaOH and $CH_2Cl_2$. The aqueous phase was extracted three times with $CH_2Cl_2$, and the combined organic phases were dried ($MgSO_4$), filtered and evaporated. Subsequent chromatography (silica gel, $CH_2Cl_2$/MeOH 19:1) yielded 0.61 g (92%) of ethyl 2-[3-benzenesulphonyl-5-methyl-7-(4-methyl-piperazin-1-yl) -pyrazolo[1,5-a]pyrimidin-2-yloxy]-acetate as a colorless foam.

e) A solution of 0.126 g of KOH in 5 ml of $H_2O$ was added to a solution of 0.61 mg of ethyl 2-[3-benzenesulphonyl-5-methyl-7-(4-methyl-piperazin-1-yl)-pyrazolo[1,5-a]pyrimidin-2-yloxy]-acetate in 20 ml of dioxan/THF 1:1 and stirred at RT for 2.5 hrs. The reaction solution was evaporated and the residue was partitioned between $H_2O$ and $CH_2Cl_2$. The aqueous phase was washed three times with 30 ml of $CH_2Cl_2$,and the combined organic phases were dried ($MgSO_4$), filtered and evaporated. Chromatography ($SiO_2$, $CH_2Cl_2$/MeOH 9:1) of the residue and crystallization from EtOH yielded 0.18 g (18%) of 2-[3-benzenesulphonyl-5-methyl-7-(4-methyl-piperazin-1-yl)-pyrazolo[1,5-a]pyrimidin-2-yloxy]-ethanol as colorless crystals. M.p. 177.5–178°.

EXAMPLE 96

3-Benzenesulphonyl-5-(2-methoxy-ethyl)-2-methylsulphanyl-7-piperazin-1-yl-pyrazolo[1,5-a]pyrimidine a) A solution of 2.69 g (10 mmol) of 4-benzenesulphonyl-5-methylsulphanyl-2H-pyrazol-3-ylamine and 1.6 g (10 mmol) of methyl 5-methoxy-3-oxo-valerate in 10 ml of acetic acid was heated at reflux for 4 hrs. The reaction solution was evaporated and the residue was partitioned between $H_2O$ and $CH_2Cl_2$. The aqueous phase was extracted three times with 80 ml of $CH_2Cl_2$. The combined organic phases were dried ($MgSO_4$), filtered and evaporated. Chromatography ($SiO_2$, $CH_2Cl_2$/MeOH 20:1) yielded 2.40 g (61%) of 3-benzenesulphonyl-5-(2-methoxy-ethyl)-2-methylsulphanyl-pyrazolo[1,5-a]pyrimidin-7-ol as a beige powder.

b) A suspension of 2.3 g (6.0 mmol) of 3-benzenesulphonyl-5-(2-methoxy-ethyl)-2-methylsulphanyl-pyrazolo[1,5-a]pyrimidin-7-ol in 40 ml of $POCl_3$ and 20 ml of diethylaniline was heated at reflux for 1 hr. The reaction solution was cooled to RT and evaporated. The residue was treated with 100 ml of ice-water and the pH value of the solution was adjusted to 8 with sat. $NaHCO_3$ solution. The aqueous phase was extracted three times with 100 ml of $CH_2Cl_2$, and the organic phases were dried ($MgSO_4$), filtered and evaporated. Chromatography ($SiO_2$, $CH_2Cl_2$/MeOH 200:1) of the residue yielded 1.8 g (75%) of 3-benzenesulphonyl-7-chloro-5-(2-methoxy-ethyl)-2-methylsuphanyl-pyrazolo-[1,5-a]pyrimidine as a pale yellow powder.

c) 0.4 g (4.8 mmol) of piperazine in 3 ml of DMF was added to a solution of 0.35 g (0.8 mmol) of 3-benzenesulphonyl-7-chloro-5-(2-methoxy-ethyl)-2-methylsuphanyl-pyrazolo-[1,5-a]pyrimidine in 10 ml of DMF and stirred at RT for 2 hrs. The reaction solution was evaporated, the residue was partitioned between 2N NaOH and $CH_2Cl_2$. The aqueous phase was extracted three times with $CH_2Cl_2$, the combined organic phases were dried ($MgSO_4$), filtered and evaporated. Subsequent chromatography ($SiO_2$, $CH_2Cl_2$/MeOH 8:1) and crystalliazation from EtOH yielded 0.25 g (62%) of 3-benzenesuphonyl-5-(2-methoxy-ethyl)-2-methylsulphanyl-7-piperazin-1-yl-pyrazolo[1,5-a]pyrimidine as colorless crystals, m.p. 155–156°.

EXAMPLE 97

3-Benzenesulphonyl-5-(2-methoxy-ethyl)-7-(4-methyl-piperazin-1-yl)-2-methylsulphanyl-pyrazolo[1,5-a]pyrimidine 0.5 g (5 mmol) of 1-methyl-piperazine in 3 ml of DMF was added to a solution of 0.45 g (1.13 mmol) of 3-benzenesulphonyl-7-chloro-5-(2-methoxy-ethyl)-2-methylsulphanyl-pyrazolo[1,5-a]pyrimidine in 20 ml of DMF and stirred at RT for 3 hrs. The reaction solution was evaporated, the residue was partitioned between 2N NaOH and $CH_2Cl_2$. The aqueous phase was extracted three times with $CH_2Cl_2$, the combined organic phases were dried (MgSO4), filtered and evaporated. Subsequent chromatography (silica gel, $CH_2Cl_2$/MeOH 12:1) and crystallization from EtOH yielded 0.255 g (67%) of 3-benzenesulphonyl-5-(2-methoxy-ethyl)-7-(4-methyl-piperazin-1-yl)-2-methylsulphanyl-pyrazolo[1,5-a]-pyrimidine as colorless crystals, m.p. 160–161°.

EXAMPLE 98

3-Benzenesulphonyl-5-(2-methoxy-ethyl)-2-methylsulphanyl-pyrazolo[1,5-a]pyrimidin-7-ylamine 10 ml of a 50% solution of $NH_3$ in MeOH were added to a solution of 0.50 g (1.25 mmol) of 3-benzenesulphonyl-7-chloro-5-(2-methoxy-ethyl)-2-methylsulphanyl-pyrazolo[1,5-a]-pyrimidine in 10 ml of DMF and stirred at RT for 2 hrs. The reaction solution was evaporated in a high vacuum and the residue was partitioned between 2N NaOH and $CH_2Cl_2$. The aqueous phase was extracted three times with $CH_2Cl_2$ and the combined organic phases were dried ($MgSO_4$), filtered and evaporated. Subsequent chromatography ($SiO_2$, $CH_2Cl_2$/MeOH 10:1) and crystallization from EtOH yielded 0.30 g (63%) of 3-benzenesulphonyl-5-(2-methoxy-ethyl)-2-methylsulphanyl-pyrazolo[1,5-a]pyrimidin-7-ylamine as colorless crystals, m.p. 186–187°.

EXAMPLE 99

3-Benzenesulphonyl-5-(2-methoxy-ethyl)-2-methylsulphanyl-7-piperazin-1-yl-pyrazolo[1,5-a]pyrimidine a) A solution of 2.69 g (10 mmol) 4-benzenesulphonyl-5-methylsulphanyl-2H-pyrazol-3-ylamine and 1.46 g (10 mmol) of ethyl 4-methoxy-acetoacetate in 10 ml of acetic acid was heated at reflux for 3 hrs. The reaction solution was evaporated and the residue was partitioned between $H_2O$ and $CH_2Cl_2$. The aqueous phase was extracted three times with 80 ml of $CH_2Cl_2$. The combined organic phases were dried ($MgSO_4$), filtered and evaporated. Chromatography ($SiO_2$, $CH_2Cl_2$/MeOH 25:1) yielded 3.1 g (85%) of 3-benzenesulphonyl-5-methoxymethyl-2-methylsulphanyl-pyrazolo[1,5-a]pyrimidin-7-ol as a beige powder, m.p. 175–155°.

b) A suspension of 2.5 g (6.8 mmol) of 3-benzenesulphonyl-5-methoxymethyl-2-methylsulphanyl-pyrazolo[1,5-a]pyrimidin-7-ol in 40 ml of $POCl_3$ and 20 ml of diethylaniline was heated at reflux for 1 hr. The reaction solution was cooled to RT and evaporated. The residue was treated with 100 ml of ice-water and the pH value of the solution was adjusted to 8 with sat. $NaHCO_3$ solution. The aqueous phase was extracted three times with 100 ml of $CH_2Cl_2$, and the organic phases were dried ($MgSO_4$), filtered and evaporated. Chromatography ($SiO_2$, $CH_2Cl_2$/MeOH 20:1) yielded 2.1 g (79%) of 3-benzenesulphonyl-7-chloro-5-methoxymethyl-2-methylsulphanyl-pyrazolo[1,5-a]pyrimidine as a pale yellow powder, m.p. 194–197°.

c) 0.4 g (4.8 mmol) of piperazine in 3 ml of DMF was added to a solution of 0.50 g (1.13 mmol) of 3-benzenesulphonyl-7-chloro-5-methoxymethyl-2-methylsulphanyl-pyrazolo[1,5-a]pyrimidine in 15 ml of DMF and stirred at RT for 2 hrs. The reaction solution was evaporated and the residue was partitioned between 2N NaOH and $CH_2Cl_2$. The aqueous phase was extracted three times with $CH_2Cl_2$, and the combined organic phases were dried ($MgSO_4$), filtered and evaporated. Subsequent chromatography ($SiO_2$, $CH_2Cl_2$/MeOH 8:1) and crystallization from EtOH yielded 0.42 g (74%) of 3-benzenesulphonyl-5-(2-methoxy-ethyl)-2-methylsulphanyl-7-piperazin-1-yl-pyrazolo[1,5-a]pyrimidine as colorless crystals, m.p. 170–171°.

EXAMPLE 100

3-Benzenesulphonyl-5-methoxymethyl-7-(4-methyl-piperazin-1-yl)-2-methylsulphanyl-pyrazolo[1,5-a]pyrimidine 0.50 g (5 mmol) of 1-methyl-piperazine in 3 ml of DMF was added to a solution of 0.50 g (1.3 mmol) of 3-benzenesulphonyl-7-chloro-5-methoxymethyl-2-methylsulphanyl-pyrazolo[1,5-a]pyrimidine in 15 ml of DMF and stirred at RT for 2 hrs. The reaction solution was evaporated and the residue was partitioned between 2N NaOH and $CH_2Cl_2$. The aqueous phase was extracted three times with $CH_2Cl_2$, and the combined organic phases were dried ($MgSO_4$), filtered and evaporated. Subsequent chromatography ($SiO_2$, $CH_2Cl_2$/MeOH 10:1) and crystallization from EtOH yielded 0.42 g (72%) of 3-benzenesulphonyl-5-methoxy-methyl-7-(4-methyl-piperazin-1-yl)-2-methylsulphanyl-pyrazolo-[1,5-a]pyrimidine as colorless crystals, m.p. 207–208°.

EXAMPLE 101

3-Benzenesulphonyl-5-methoxymethyl-2-methylsulphanyl-pyrazolo[1,5-a]pyrimidin-7-ylamine 10 ml of a 50% solution of $NH_3$ in MeOH was added to a solution of 0.50 g (1.3 mmol) of 3-benzenesulphonyl-7-chloro-5-methoxymethyl-2-methylsulphanyl-pyrazolo[1,5-a]-pyrimidine in 10 ml of DMF and stirred at RT for 2 hrs. The reaction solution was evaporated and the residue was partitioned between 2N NaOH and $CH_2Cl_2$. The aqueous phase was extracted three times with $CH_2Cl_2$, and the combined organic phases were dried ($MgSO_4$), filtered and evaporated. Subsequent chromatography ($SiO_2$, $CH_2Cl_2$/MeOH 10:1) and crystallization from EtOH yielded 0.38 g (80%) of 3-benzenesulphonyl-5-methoxymethyl-2-methylsulphanyl-pyrazolo[1,5-a]pyrimidin-7-ylamine as colorless crystals, m.p.>230°.

EXAMPLE 102

3-Benzenesulphonyl-5-chloro-7-(4-methyl-piperazin-1-yl)-2-methylsulphanyl-pyrazolo[1,5-a]pyrimidine a) 5.38 g (20 mmol) of 4-benzenesulphonyl-5-methylsulphanyl-2H-pyrazol-3-ylamine followed by 9 ml (60 mmol) of diethyl malonate were added to a freshly prepared solution of sodium ethanolate in EtOH (prepared from 0.89 g (77 mmol) of sodium in 100 ml of EtOH) and the mixture was heated at reflux for 48 hrs. After cooling to RT the mixture was subsequently poured on to 140 ml of ice-water. The resulting precipitate was filtered off and dried at 500 in a high vacuum. There were thus obtained 6.5 g (96%) of 3-benzenesulphonyl-2-methylsulphanyl-pyrazolo[1,5-a]pyrimidine-5,7-diol as a beige powder, m.p. >230°.

b) A suspension of 3.0 g (8.89 mmol) of 3-benzenesulphonyl-2-methylsulphanyl-pyrazolo[1,5-a]pyrimidine-5,7-diol in 40 ml of $POCl_3$ was heated at reflux for 1 hr. The reaction solution was cooled to RT and evaporated. The residue was treated with 100 ml of ice-water and the pH value of the solution was adjusted to 8 with sat. $NaHCO_3$ solution. The aqueous phase was extracted three times with 90 ml of $CH_2Cl_2$, and the organic phases were dried ($MgSO_4$), filtered and evaporated. Chromatography ($SiO_2$, $CH_2Cl_2$/AcOEt 1.5:1) of the residue yielded 1.8 g (54%) of 3-benzenesulphonyl-5,7-dichloro-2-methylsulphanyl-pyrazolo[1,5-a]pyrimidine as colorless crystals, m.p. 193–197°.

c) 0.1 g (1 mmol) of 1-methyl-piperazine in 3 ml of $CH_2Cl_2$ was added to a solution of 0.37 g (1 mmol) of 3-benzenesulphonyl-5,7-dichloro-2-methylsulphanyl-pyrazolo[1,5-a]-pyrimidine in 20 ml of $CH_2Cl_2$ and stirred at RT for 1 hr. The mixture was poured on to ice-water, adjusted to pH8 with $NaHCO_3$ solution and extracted three times with 30 ml of $CH_2Cl_2$. The combined organic phases were dried ($MgSO_4$), filtered and evaporated. Subsequent chromatography (silica gel, $CH_2Cl_2$/MeOH 4:1) yielded 0.38 g (86%) of 3-benzenesulphonyl-5-chloro-7-(4-methyl-piperazin-1-yl)-2-methylsulphanyl-pyrazolo[1,5-a]pyrimidine as colorless crystals, m.p.>230°.

EXAMPLE 103

3-Benzenesulphonyl-7-(4-methyl-piperazin-1-yl)-2-methylsulphanyl-pyrazolo[1.5-a]-pyrimidine 0.15 g of Pd/C (10%) and 0.3 ml of $NEt_3$ were added to a solution of 0.189 g (0.4 mmol) of 3-benzenesulphonyl-5-chloro-7-(4-methyl-piperazin-1-yl)-2-methylsulphanyl-pyrazolo[1,5-a]pyrimidine in 30 ml of EtOH and hydrogenated at RT for 12 hrs. The reaction mixture was filtered over Dicalite and the filtrate was evaporated. Chromatography of the residue ($SiO_2$, $CH_2Cl_2$/MeOH 20:1) yielded 0.08 g (49%) of 3-benzenesulphonyl-7-(4-methyl-piperazin-1-yl)-2-methylsulphanyl-pyrazolo[1,5-a]pyrimidine as colorless crystals, m.p. 107–109°.

EXAMPLE 104

2-[3-Benzenesulphonyl-7-(4-methyl-piperazin-1-yl)-2-methylsulphanyl-pyrazolo[1,5-a]pyrimidin-5-yloxy]-ethanol 0.115 g (5 mmol) of sodium was added to 20 ml of ethylene glycol and this solution was treated with 0.22 g (0.5 mmol) of 3-benzenesulphonyl-5-chloro-7-(4-methyl-piperazin-1-yl)-2-methylsulphanyl-pyrazolo[1,5-a]pyrimidine and subsequently stirred at 80° for 1 hr. After cooling to RT the reaction solution was poured on to 70 ml of ice-water and extracted three times with 50 ml of AcOEt. The combined organic phases were dried ($MgSO_4$), filtered and evaporated. Chromatography ($SiO_2$, $CH_2Cl_2$/MeOH/$NH_4OH$ 110:10:1) of the residue and crystallization from EtOH yielded 0.16 g (69%) of 2-[3-benzenesulphonyl-7-(4-methylpiperazin-1-yl)-2-methylsulphanyl-pyrazolo[1,5-a]pyrimidin-5-yloxy]-ethanol as colorless crystals, m.p. 187–189°.

EXAMPLE 105

3-Benzenesulphonyl-5-chloro-2-methylsulphanyl-pyrazolo[1,5-a]pyrimidin-7-ylamine 10 ml of a 50% solution of $NH_3$ in MeOH were added to a solution of 0.35 g (0.935 mmol) of 3-benzenesulphonyl-5,7-dichloro-2-methylsulphanyl-pyrazolo[1,5-a]pyrimidine in 10 ml of DMF and stirred at RT for 12 hrs. The DMF was evaporated in a high vacuum and the residue was partitioned between 2N NaOH and $CH_2Cl_2$. The aqueous phase was extracted three times with $CH_2Cl_2$, and the combined organic phases were dried ($MgSO_4$), filtered and evaporated. Subsequent chromatography (silica gel, $CH_2Cl_2$/AcOEt 15:1) and crystallization from EtOH yielded 0.28 g (84%) of 3-benzenesulphonyl-5-chloro-2-methylsulphanyl-pyrazolo[1,5-a]pyrimidin-7-ylamine as colorless crystals, m.p.>230°.

EXAMPLE 106

3-Benzenesulphonyl-N5,N5-dimethyl-2-methylsulphanyl-pyrazolo[1,5-a]pyrimidine-5,7-diamine and 3-benzenesulphonyl-N5-(2-dimethylamino-ethyl)-2-methylsulphanyl-pyrazolo[1,5-a]pyrimidine-5,7-diamine 0.26 g (3 mmol) of 2-dimethylaminoethylamine in 5 ml of DMF was added to a solution of 0.4 g (1 mmol) of 3-benzenesulphonyl-5-chloro-2-methylsulphanyl-pyrazolo[1,5-a]pyrimidin-7-ylamine in 10 ml of DMF and stirred at 90° for 1 hr. The reaction solution was evaporated and the residue was partitioned between $H_2O$ and $CH_2Cl_2$. The aqueous phase was extracted three times with 50 ml of $CH_2Cl_2$. The combined organic phases were dried ($MgSO_4$), filtered and evaporated. Subsequent chromatography (silica gel, $CH_2Cl_2$/MeOH 8:1) yielded 0.20 g (48%) of 3-benzenesulphonyl-N5,N5-dimethyl-2-methylsulphanyl-pyrazolo[1,5-a]pyrimidine-5,7-diamine as colorless crystals, m.p.>230°, and 0.08 g (17%) of 3-benzenesulphonyl-N5-(2-dimethylamino-ethyl)-2-methylsulphanyl-pyrazolo[1,5-a]pyrimidine-5,7-diamine as colorless crystals, m.p. 210–212°.

EXAMPLE 107

3-Benzenesulphonyl-5-(4-methyl-piperazin-1-yl)-2-methylsulphanyl-pyrazolo[1,5-a]pyrimidin-7-ylamine 0.1 g (1 mmol) of 1-methyl-piperazine was added to a solution of 0.14 g (0.4 mmol) of 3-benzenesulphonyl-5-chloro-2-methylsulphanyl-pyrazolo[1,5-a]pyrimidin-7-ylamine in 5 ml of DMF and stirred at 90° for 1 hr. The reaction solution was evaporated and the residue was partitioned between $H_2O$ and $CH_2Cl_2$. The aqueous phase was extracted three times with 50 ml of $CH_2Cl_2$. The combined organic phases were dried ($MgSO_4$), filtered and evaporated. Subsequent chromatography (silica gel $CH_2Cl_2$/MeOH 9:1) and crystallization from EtOH yielded 0.1 g (59%) of 3-benzenesulphonyl-5-(4-methyl-piperazin-1-yl)-2-methylsulphanyl-pyrazolo[1,5-a]pyrimidin-7-ylamine as colorless crystals, m.p.>230°.

EXAMPLE 108

3-Benzenesulphonyl-5-chloro-2-ethyl-7-(4-methyl-piperazin-1-yl)-pyrazolo[1,5-a]-pyrimidine a) 7.90 g (31.4 mmol) of 4-benzenesulphonyl-5-ethyl-2H-pyrazol-3-ylamine followed by 14.3 ml (94.3 mmol) of diethyl malonate were added to a freshly prepared solution of sodium ethanolate in EtOH (prepared from 2.7 g (119.5 mmol) of sodium in 320 ml of EtOH) and heated at reflux for 48 hrs. After cooling to RT the mixture was subsequently poured into 140 ml of ice-water. The resulting precipitate was filtered off and dried at 50° in a high vacuum. There were thus obtained 4.8 g (48%) of 3-benzenesulphonyl-2-ethyl-pyrazolo-[1,5-a]pyrimidine-5,7-diol, m.p.>230°.

b) A suspension of 2.8 g (8.8 mmol) of 3-benzenesulphonyl-2-ethyl-pyrazolo1,5-a]pyrimidine-5,7-diol in 30 ml of $POCl_3$ was heated at reflux for 1 hr. The reaction solution was cooled to RT and evaporated. The residue was treated with 100 ml of ice-water and the pH value of the solution was adjusted to 8 with sat. $NaHCO_3$ solution. The aqueous phase was extracted three times with 100 ml of $CH_2Cl_2$, and the organic phases were dried ($MgSO_4$), filtered and evaporated. Chromatography ($SiO_2$, $CH_2Cl_2$) of the residue yielded 1.1 g (35%) of 3-benzenesulphonyl-5,7-dichloro-2-ethyl-pyrazolo[1,5-a]pyrimidine as a colorless solid.

c) 0.86 ml (7.7 mmol) of 1-methyl-piperazine in 3 ml of $CH_2Cl_2$ was added to a solution of 2.5 g (7 mmol) of 3-benzenesulphonyl-5,7-dichloro-2-ethyl-pyrazolo[1,5-a]pyrimidine in 20 ml of $CH_2Cl_2$ and stirred at RT for 2 hrs. The reaction mixture was poured on to ice-water, adjusted to pH 8 with $NaHCO_3$ solution and extracted three times with $CH_2Cl_2$. The combined organic phases were dried ($MgSO_4$), filtered and evaporated. Subsequent chromatography (silica gel, $CH_2Cl_2$/MeOH 4:1) and crystallization from EtOH yielded 2.5 g (85%) of 3-benzenesulphonyl-5,7-dichloro-2-ethyl-pyrazolo[1,5-a]pyrimidine as colorless crystals, m.p. 166–167°.

EXAMPLE 109

3-Benzenesulphonyl-2-ethyl-7-(4-methyl-piperazin-1-yl)-pyrazolo[1,5-a]pyrimidine 0.1 g of Pd/C (10%) was added to a solution of 0.267 g (0.63 mmol) of 3-benzenesulphonyl-5-chloro-2-ethyl-7-(4-methyl-piperazin-1-yl)-pyrazolo[1,5-a]pyrimidine in 40 ml of EtOH and the mixture was hydrogenated at RT for 4 hrs. The reaction mixture was filtered over Dicalite and the filtrate was evaporated. The residue was partitioned between $CH_2Cl_2$ and sat. $NaHCO_3$ solution. The aqueous phase was extracted three times with $CH_2Cl_2$. The combined organic phases were dried ($MgSO_4$), filtered and evaporated. Chromatography of the residue ($SiO_2CH_2Cl_2$/MeOH 19:1) and crystallization from EtOH yielded 0.2 g (53%) of as pale beige crystals, m.p. 206–207°.

EXAMPLE 110

3-Benzenesulphonyl-2-ethyl-5,7-bis-(4-methyl-piperazin-1-yl)-pyrazolo[1,5-a]pyrimidine 0.33 ml (3 mmol) of 1-methyl-piperazine in 5 ml of DMF was added to a solution of 0.50 g (1.2 mmol) of 3-benzenesulphonyl-5-chloro-2-ethyl-7-(4-methyl-piperazin-1-yl)-pyrazolo[1,5-a]pyrimidine in 15 ml of DMF and stirred at 100° for 1 hr. After cooling to RT the reaction solution was evaporated and the residue was partitioned between 2N NaOH and $CH_2Cl_2$. The aqueous phase was extracted three times with $CH_2Cl_2$, and the combined organic phases were dried ($MgSO_4$), filtered and evaporated. Subsequent chromatography ($SiO_2$, $CH_2Cl_2$/MeOH/$NH_4OH$ 110:10:1) and crystallization from EtOH yielded 0.04 g (69%) of 3-benzenesulphonyl-2-ethyl-5,7-bis-(4-methyl-piperazin-1-yl)-pyrazolo[1,5-a]pyrimidine as colorless crystals, m.p. 232–235°.

EXAMPLE 111

3-Benzenesulphonyl-2-ethyl-7-(4-methyl-piperazin-1-yl)-5-morpholin-4-yl-pyrazolo[1,5-a]-pyrimidine 0.26 ml (3 mmol) of morpholine in 5 ml of DMF was added to a solution of 0.50 g (1.2 mmol) of 3-benzenesulphonyl-5-chloro-2-ethyl-7-(4-methyl-piperazin-1-yl)-pyrazolo[1,5-a]pyrimidine in 15 ml of DMF and stirred at 100° for hr. After cooling to RT the reaction solution was evaporated and the residue was partitioned between 2N NaOH and $CH_2Cl_2$. The aqueous phase was extracted three times with $CH_2Cl_2$, and the combined organic phases were dried ($MgSO_4$), filtered and evaporated. Subsequent chromatography ($SiO_2$, $CH_2Cl_2$/MeOH 15:1)

and crystallization from EtOH yielded 0.45 g (80%) of 3-benzenesulphonyl-2-ethyl-7-(4-methyl-piperazin-1-yl)-5-morpholin-4-yl-pyrazolo[1,5-a]-pyrimidine as colorless crystals, m.p.>250°.

EXAMPLE 112

2-[3-Benzenesulphonyl-2-ethyl-7-(4-methyl-piperazin-1-yl)-pyrazolo[1,5-a]pyrimidin-5-yl-oxy]-ethanol 0.274 g (12 mmol) of sodium was added to 40 ml of ethylene glycol and this solution was treated with 0.50 g (1.2 mmol) of 3-benzenesulphonyl-5-chloro-2-ethyl-7-(4-methyl-piperazin-1-yl)-pyrazolo[1,5-a]pyrimidine and subsequently stirred at 80° for 1 hr. After cooling to RT the reaction solution was poured on to 70 ml of ice-water and extracted three times with 50 ml of AcOEt. The combined organic phases were dried (MgSO$_4$), filtered and evaporated. Chromatography (SiO$_2$, CH$_2$Cl$_2$/MeOH 9:1) of the residue and crystallization from EtOH yielded 0.24 g (44%) of 2-[3-benzenesulphonyl-2-ethyl-7-(4-methyl-piperazin-1-yl)-pyrazolo[1,5-a]pyrimidin-5-yl-oxy]-ethanol as colorless crystals, m.p. 153–154°.

EXAMPLE 113

[3-Benzenesulphonyl-2-ethyl-7-(4-methyl-piperazin-1-yl)-pyrazolo[1,5-a]pyrimidin-5-yl]-dimethyl-amine and N-[3-benzenesulphonyl-2-ethyl-7-(4-methyl-piperazin-1-yl)-pyrazolo[1,5-a]pyrimidin-5-yl]-N',N'-dimethyl-ethane-1,2-diamine 0.72 g (6.5 mmol) of 2-dimethylaminoethylamine in 5 ml of DMF was added to a solution of 1.1 g (2.6 mmol) of 3-benzenesulphonyl-5-chloro-2-ethyl-7-(4-methyl-piperazin-1-yl)-pyrazolo[1,5-a]pyrimidine in 20 ml of DMF and stirred at 90° for 1 hr. After cooling to RT the reaction solution was evaporated and the residue was partitioned between 2N NaOH and CH$_2$Cl$_2$. The aqueous phase was extracted three times with 80 ml of CH$_2$Cl$_2$. The combined organic phases were dried (MgSO$_4$), filtered and evaporated. Subsequent chromatography (silica gel, CH$_2$Cl$_2$/MeOH/NH$_4$OH 65:10:1) yielded 0.20 g (13%) of [3-benzenesulphonyl-2-ethyl-7-(4-methyl-piperazin-1-yl)-pyrazolo[1,5-a]pyrimidin-5-yl]-dimethyl-amine as colorless crystals, m.p. 211–212°, and 0.30 g (24%) of N-[3-benzenesulphonyl-2-ethyl-7-(4-methyl-piperazin-1-yl)-pyrazolo[1,5-a]pyrimidin-5-yl]-N',N'-dimethyl-ethane-1,2-diamine as colorless crystals, m.p. 163–164°.

EXAMPLE 114

3-Benzenesulphonyl-5-chloro-2-ethyl-pyrazolo[1,5-a]pyrimidin-7-ylamine 20 ml of a 50% solution of NH$_3$ in MeOH were added to a solution of 1.1 g (3.1 mmol) of 3-benzenesulphonyl-2-ethyl-pyrazolo[1,5-a]pyrimidine-5,7-diol in 10 ml of DMF and stirred at RT for 12 hrs. The reaction solution was evaporated and the residue was partitioned between 2N NaOH and CH$_2$Cl$_2$. The aqueous phase was extracted three times with CH$_2$Cl$_2$ and the combined organic phases were dried (MgSO$_4$), filtered and evaporated. The residue was treated with 5 ml of EtOH and the crystals obtained were filtered off. There was thus obtained 0.80 g (77%) of 3-benzenesulphonyl-5-chloro-2-ethyl-pyrazolo[1,5-a]-pyrimidin-7-ylamine as colorless crystals, m.p.>220°.

EXAMPLE 115

3-Benzenesulphonyl-2-ethyl-5-(4-methyl-piperazin-1-yl)-pyrazolo[1,5-a]pyrimidin-7-yl-amine 0.33 ml (3 mmol) of 1-methyl-piperazine was added to a solution of 0.4 g (1.2 mmol) of 3-benzenesulphonyl-5-chloro-2-ethyl-pyrazolo[1,5-a]pyrimidin-7-ylamine in 5 ml of DMF and stirred at 90° for 1 hr. The reaction solution was evaporated and the residue was partitioned between H$_2$O and CH$_2$Cl$_2$. The aqueous phase was extracted three times with 50 ml of CH$_2$Cl$_2$. The combined organic phases were dried (MgSO$_4$), filtered and evaporated. Subsequent chromatography (silica gel, CH$_2$Cl$_2$/MeOH 9:1) and crystallization from EtOH yielded 0.24 g (50%) of 3-benzenesulphonyl-2-ethyl-5-(4-methyl-piperazin-1-yl)-pyrazolo[1,5-a]pyrimidin-7-yl-amine as colorless crystals, m.p.>250°.

EXAMPLE 116

3-Benzenesulphonyl-2-ethyl-N5,N5-dimethyl-pryazolo[1,5-a]pyrimidine-5,7-diamine and 3-benzenesulphonyl-N5-(2-dimethylamino-ethyl)-2-ethyl-pyrazolo[1,5-a]pyrimidine-5,7-diamine 0.73 g (6.68 mmol) of 2-dimethylaminoethylamine in 5 ml of DMF was added to a solution of 0.45 g (1.3 mmol) of 3-benzenesulphonyl-5-chloro-2-ethyl-pyrazolo[1,5-a] pyrimidin-7-ylamine in 10 ml of DMF and stirred at 90° for 1 hr. The reaction solution was evaporated and the residue was partitioned between H$_2$O and CH$_2$Cl$_2$. The aqueous phase was extracted three times with 80 ml of CH$_2$Cl$_2$. The combined organic phases were dried (MgSO$_4$), filtered and evaporated. Subsequent chromatography (silica gel, CH$_2$Cl$_2$/MeOH/NH$_4$OH 65:10:1) yielded 0.12 g (26%) 3-benzenesulphonyl-2-ethyl-N5,N5-dimethyl-pyrazolo[1,5-a]pyrimidine-5,7-diamine as colorless crystals, m.p. 228–230°, and 0.09 g (17 %) 3 -benzenesulphonyl-N5-(2-dimethylamino-ethyl)-2-ethyl-pyrazolo[1,5-a]pyrimidine-5, 7-diamine as colorless crystals, m.p. 149.5–150.5°.

EXAMPLE 117

3-Benzenesulphonyl-5-dimethylaminomethyl-2-methylsulphanyl-pyrazolo[1,5-a]pyrimidin-7-ylamine a) 6.8 ml (50 mmol) of ethyl 4-chloro-acetoacoacetate were added to a solution of 13.5 mmol (50 mmol) of 4-benzenesulphonyl-5-methylsulphanyl-2H-pyrazol-3-ylamine in 80 ml of acetic acid and heated at reflux for 1.5 hrs. After cooling to RT the crystals obtained were filtered off, washed with EtOH and dried in a high vacuum at 500. There were thus obtained 10.5 g (56%) of 3-benzenesulphonyl-5-chloromethyl-2-methylsulphanyl-pyrazolo[1,5-a]pyrimidin-7-ol as a colorless powder, m.p. 215–217°.

b) 5 ml of a 33% solution of dimethylamine in EtOH were added to a solution of 1.4 g (3.7 mmol) of 3-benzenesulphonyl-5-chloromethyl-2-methylsulphanyl-pyrazolo[1,5-a]pyrimidin-7-ol in 20 ml of DMF and stirred at RT for 4 hrs. The reaction solution was evaporated, the residue was partitioned between 0.5N NaOH and CH$_2$Cl$_2$. The aqueous phase was extracted three times with CH$_2$Cl$_2$. The combined organic phases were dried (MgSO$_4$), filtered and evaporated. Chromatography (SiO$_2$, CH$_2$Cl$_2$/MeOH 4:1) yielded 1.3 g (92%) of 3-benzenesulphonyl-5-dimethylaminomethyl-2-methylsulphanyl-pyrazolo[1,5-a] pyrimidin-7-ol as a beige powder, m.p.>220°.

c) A suspension of 1.3 g (3.43 mmol) of 3-benzenesulphonyl-5-dimethylaminomethyl-2-methylsulphanyl-pyrazolo[1,5-a]pyrimidin-7-ol in 50 ml of POCl$_3$ was heated at reflux for 3 hrs. The reaction solution was cooled to RT and evaporated. The residue was treated with 100 ml of ice-water and the pH value of the solution was adjusted to 8 with sat. NaHCO$_3$ solution. The aqueous phase was extracted three times with 100 ml of CH$_2$Cl$_2$ and the organic phases were dried (MgSO$_4$), filtered and evaporated. Chromatography (SiO$_2$, CH$_2$Cl$_2$/AcOEt 1:1) of the residue yielded 1.2 g (88%) of (3-benzenesulphonyl-7-chloro-2-methylsulphanyl-pyrazolo[1,5-a]pyrimidin-5-ylmethyl)-dimethyl-amine as a colorless foam.

d) 20 ml of a 50% solution of NH$_3$ in MeOH were added to a solution of 1.20 g (3 mmol) of (3-benzenesulphonyl-7-chloro-2-methylsulphanyl-pyrazolo[1,5-a]pyrimidin-5-ylmethyl)-dimethyl-amine in 30 ml of DMF and stirred at RT for 4 hrs. The reaction solution was evaporated and the residue was partitioned between 2N NaOH and CH$_2$Cl$_2$. The aqueous phase was extracted three times with CH$_2$Cl$_2$, and the combined organic phases were dried (MgSO$_4$), filtered and evaporated. Subsequent chromatography (silica gel, CH$_2$Cl$_2$/MeOH 6:1) yielded 0.90 g (78%) of 3-benzenesulphonyl-5-dimethylaminomethyl-2-methylsulphanyl-pyrazolo[1,5-a]pyrimidin-7-ylamine as colorless crystals, m.p. 216–218°.

EXAMPLE 118

3-Benzenesulphonyl-5-(4-methyl-piperazin-1-ylmethyl)-2-methylsulphanyl-pyrazolo[1,5-a]pyrimidin-7-ylamine a) 1.57 ml (15.70 mml) of 1-methyl-piperazine were added to a solution of 2.9 g (7.84 mmol) of 3-benzenesulphonyl-5-chloromethyl-2-methylsulphanyl-pyrazolo[1,5-a]pyrimidin-7-ol in 20 ml of DMF and stirred at RT for 4 hrs. The reaction solution was evaporated and the residue was partitioned between 0.5N NaOH and CH$_2$Cl$_2$. The aqueous phase was extracted three times with CH$_2$Cl$_2$. The combined organic phases were dried (MgSO$_4$), filtered and evaporated. Chromatography (SiO$_2$, CH$_2$Cl$_2$/MeOH 4:1) yielded 1.85 g (53%) of 3-benzenesulphonyl-5-(4-methyl-piperazin-1-ylmethyl)-2-methylsulphanyl-pyrazolo[1,5-a]pyrimidin-7-ol as a beige powder, m.p.>220°.

b) A suspension of 4.0 g (9 mmol) of 3-benzenesulphonyl-5-(4-methyl-piperazin-1-ylmethyl)-2-methylsulphanyl-pyrazolo[1,5-a]pyrimidin-7-ol in 100 ml of POCl$_3$ was heated at reflux for 3 hrs. The reaction solution was cooled to RT and evaporated. The residue was treated with 100 ml of ice-water and the pH value of the solution was adjusted to 8 with sat. NaHCO$_3$ solution. The aqueous phase was extracted three times with 150 ml of CH$_2$Cl$_2$ and the organic phases were dried (MgSO$_4$), filtered and evaporated. Chroma-tography (SiO$_2$CH$_2$Cl$_2$/MeOH 10:1) of the residue yielded 4.0 g (98%) of 3-benzenesulphonyl-7-chloro-5-(4-methyl-piperazin-1-ylmethyl)-2-methylsulphanyl-pyrazolo[1,5-a]pyrimidine as a pale brown powder, m.p. 113–116°.

c) 10 ml of a 50% solution of NH$_3$ in MeOH were added to a solution of 0.8 g (1.77 mmol) of 3-benzenesulphonyl-7-chloro-5-(4-methyl-piperazin-1-ylmethyl)-2-methylsulphanyl-pyrazolo[1,5-a]pyrimidine in 20 ml of DMF and stirred at RT for 4 hrs. The reaction solution was evaporated and the residue was partitioned between 2N NaOH and CH$_2$Cl$_2$. The aqueous phase was extracted three times with CH$_2$Cl$_2$, and the combined organic phases were dried (MgSO$_4$), filtered and evaporated. Subsequent chromatography (SiO$_2$, CH$_2$Cl$_2$/MeOH/NH4OH 90:10:1) yielded 0.59 g (77%) of 3-benzenesulphonyl-5-(4-methyl-piperazin-1-ylmethyl)-2-methylsulphanyl-pyrazolo[1,5-a]pyrimidin-7-ylamine as colorless crystals, m.p. 203–205°.

EXAMPLE 119

3-Benzenesulphonyl-7-(4-methyl-piperazin-1-yl)-5-(4-methyl-piperazin-1-ylmethyl)-2-methylsulphanyl-pyrazolo[1,5-a]pyrimidine 0.4 g (4 mmol) of 1-methyl-piperazine was added to a solution of 0.8 g (1.77 mmol) of 3-benzenesulphonyl-7-chloro-5-(4-methyl-piperazin-1-ylmethyl)-2-methylsulphanyl-pyrazolo[1,5-a]pyrimidine in 20 ml of DMF and stirred at RT for 6 hrs. The reaction solution was evaporated and the residue was partitioned between 2N NaOH and CH$_2$Cl$_2$. The aqueous phase was extracted three times with CH$_2$Cl$_2$, and the combined organic phases were dried (MgSO$_4$), filtered and evaporated. Subsequent chromatography (SiO$_2$, CH$_2$Cl$_2$/MeOH/NH$_4$OH 80:10:1) and crystallization from EtOH yielded 0.75 g (82%) of 3-benzenesulphonyl-7-(4-methyl-piperazin-1-yl)-5-(4-methyl-piperazin-1-ylmethyl)-2-methylsulphanyl-pyrazolo[1,5-a]pyrimidine as colorless crystals, m.p. 193–195°.

EXAMPLE 120

3-Benzenesulphonyl-5-(4-methyl-piperazin-1-ylmethyl)-2-methylsulphanyl-pyrazolo 1,5-a]pyrimidin-7-ylamine a) 1 ml (6 mmol) of morpholine was added to a solution of 2.0 g (5.40 mmol) of 3-benzenesulphonyl-5-chloromethyl-2-methylsulphanyl-pyrazolo[1,5-a]pyrimidin-7-ol in 20 ml of DMF and stirred at RT for 4 hrs. The reaction solution was evaporated and the residue was partitioned between 0.5N NaOH and CH$_2$Cl$_2$. The aqueous phase was extracted three times with CH$_2$Cl$_2$. The combined organic phases were dried (MgSO$_4$), filtered and evaporated. Chromatography (SiO$_2$, CH$_2$Cl$_2$/MeOH 10:1) yielded 2.0 g (88%) of 3-benzenesulphonyl-2-methylsulphanyl-5-morpholin-4-ylmethyl-pyrazolo[1,5-a]pyrimidin-7-ol as a beige foam.

b) A suspension of 2.0 g (4.75 mmol) of 3-benzenesulphonyl-2-methylsulphanyl-5-morpholin-4-ylmethyl-pryazolo[1,5-a]pyrimidin-7-ol in 30 ml of POCl$_3$ was heated at reflux for 3 hrs. The reaction solution was cooled to RT and evaporated. The residue was treated with 100 ml of ice-water and the pH value of the solution was adjusted to 8 with sat. NaHCO$_3$ solution. The aqueous phase was extracted three times with 70 ml of CH$_2$Cl$_2$ and the organic phases were dried (MgSO$_4$), filtered and evaporated. Chromatography (SiO$_2$, CH$_2$Cl$_2$/MeOH 10:1) of the residue yielded 1.8 g (86%) of 3-benzenesulphonyl-7-chloro-2-methylsulphanyl-5-morpholin-4-ylmethyl-pyrazolo[1,5-a]pyrimidine as a pale brown powder, m.p. 174–176°.

c) 10 ml of a 50% solution of NH$_3$ in MeOH were added to a solution of 0.9 g (2 mmol) of 3-benzenesulphonyl-7-chloro-2-methylsulphanyl-5-morpholin-4-ylmethyl-pyrazolo[1,5-a]pyrimidine in 20 DMF and stirred at RT for 4 hrs. The DMF was evaporated in a high vacuum and the residue was partitioned between 2N NaOH and CH$_2$Cl$_2$. The aqueous phase was extracted three times with CH$_2$Cl$_2$ and the combined organic phases were dried (MgSO$_4$), filtered and evaporated. Subsequent chromatography (silica gel, CH$_2$Cl$_2$/MeOH/NH$_4$OH 80:10:1) and crystallization from EtOH yielded 0.70 g (83%) of 3 -benzenesulphonyl-5-(4-methyl-piperazin-1-ylmethyl)-2-methylsulphanyl-pyrazolo[1,5-a]pyrimidin-7-ylamine as colorless crystals, m.p. 224–226°.

EXAMPLE 121

3-Benzenesulphonyl-7-(4-methyl-piperazin-1-yl)-2-methylsulphanyl-5-morpholin-4-ylmethyl-pyrazolo[1,5-a]pyrimidine 0.4 g (4 mmol) of 1-methyl-piperazine was added to a solution of 0.9 g (2 mmol) of 3-benzenesulphonyl-7-chloro-2-methylsulphanyl-5-morpholin-4-ylmethyl-pyrazolo[1,5- a]pyrimidine in 20 ml of DMF and stirred at RT for 4 hrs. The reaction solution was evaporated and the residue was partitioned between 2N NaOH and $CH_2Cl_2$. The aqueous phase was extracted three times with $CH_2Cl_2$ and the combined organic phases were dried ($MgSO_4$), filtered and evaporated. Subsequent chromatography ($SiO_2$, $CH_2Cl_2$/MeOH/$NH_4OH$ 80:1:1) and crystallization from EtOH yielded 0.80 g (77%) of 3-benzenesulphonyl-7-(4-methyl-piperazin-1-yl)-2-methylsulphanyl-5-morpholin-4-ylmethyl-pyrazolo[1,5-a]pyrimidine as colorless crystals, m.p.199–201°.

EXAMPLE 122

[2-(3-Benzenesulphonyl-5-methyl-2-methylsulphanyl-pyrazolo[1,5-a]pyrimidin-7-yloxy)-ethyl]-dimethyl-amine 0.28 ml (2.38 mmol) of 2-dimethylaminoethanol and 3.68 g of $Cs_2CO_3$ were added to a solution of 0.8 g (2.26 mmol) of 3-benzenesulphonyl-7-chloro-5-methyl-2-methylsulphanyl-pyrazolo[1,5-a]pyrimidine in 40 ml of acetonitrile and the suspension was stirred at RT for 12 hrs. The reaction mixture was poured into semi-concentrated aqueous sodium chloride solution and extracted three times with ethyl acetate. The combined organic phases were dried ($MgSO_4$), filtered and evaporated. Subsequent chromatography yielded 0.65 g (70%) of 2-(3-benzenesulphonyl-5-methyl-2-methylsulphanyl-pyrazolo[1,5-a]pyrimidin-7-yloxy)-ethyl]-dimethyl-amine as a pale yellow solid, m.p. 176–178°.

EXAMPLE 123

3-Benzenesulphonyl-5-methyl-2-methylsulphanyl-7-(2-morpholin-4-yl-ethoxy)-pryazolo[1,5-a]pyrimidine In an analogous manner to that described in Example 122) from 3-benzenesulphonyl-7-chloro-5-methyl-2-methylsulphanyl-pyrazolo[1,5-a]pyrimidine and N-(2-hydroxy-ethyl)-morpholine there was obtained 3-benzenesulphonyl-5-methyl-2-methylsulphanyl-7-(2-morpholin-4-yl-ethoxy)-pyrazolo[1,5-a]pyrimidine as a pale yellow solid.

EXAMPLE 124

8-Benzenesulphonyl-7-methylsulphanyl-pryazolo[1,5-a][1,3,5]triazin-4-ylamine 0.10 g (0.37 mmol) of 5-amino-3-methylthio-4-phenylsulphonyl-pyrazole was mixed with 0.25 g (2.55 mmol) of ethyl N-cyano-methanimate and stirred at 100° C. for 16 hrs. The resulting pale beige paste was taken up in AcOEt/MeOH and treated in an ultrasound bath. The thus-obtained suspension was filtered. Chromatography ($SiO_2$, $CH_2Cl_2MeOH$ 95:5) yielded 0.052 g (44%) of 8-benzenesulphonyl-7-methylsulphanyl-pyrazolo[1,5-a][1,3,5]-triazin-4-ylamine as pale beige crystals, m.p.>280° C.

EXAMPLE 125

(8-Benzenesulphonyl-2-methyl-7-methylsulphanyl-pyrazolo[1,5-a][1,3,5]triazin-4-yl)-methylamine a) A solution of 0.54 g (2 mol) of 5-amino-3-methylthio-4-phenylsulphonyl-pyrazole and 0.54 g (3.4 mmol) of ethyl 1-ethoxy-ethylidene-carbamate in acetic acid was stirred at 100° C. for 3 hrs. After cooling to RT the precipitate was filtered off, washed off with a copious amount of $Et_2O$ and dried in a high vacuum at 45° C. There was obtained 0.41 g (61%) of 8-benzenesulphonyl-2-methyl-7-methylsulphanyl-3H-pyrazolo[1,5-a][1,3,5]-triazin-4-one white crystals, m.p.>300° C.

b) A suspension of 0.36 g (1 mmol) of 8-benzenesulphonyl-2-methyl-7-methylsulphanyl-3H-pyrazolo[1,5-a][1,3,5]triazin-4-one in 20 ml of $POCl_3$ was treated with 0.12 ml (1.5 mmol) of pyridine and heated 110° C. for 3 hrs. The reaction solution was cooled to RT and evaporated. The residue was dried azeotropically twice with 50 ml of toluene each time. The thus-obtained residue was taken in 10 ml of 2N methylamine in tetrahydrofuran and stirred at room temperature for 4 hrs. The reaction solution was evaporated and partitioned between $H_2O$ and AcOEt. The organic phase was washed with $H_2O$ and sat. NaCl solution, dried ($MgSO_4$), filtered and evaporated. Chromatography ($SiO_2$, AcOEt/hexane 1:1) yielded 0.28 g (80%) of (8-benzenesulphonyl-2-methyl-7-methylsulphanyl-pyrazolo[1,5-a][1,3,5]triazin-4-yl)-methylamine as white crystals, m.p. 285° (dec).

EXAMPLE 126

(8-Benzenesulphonyl-2-methyl-7-methylsulphanyl-pyrazolo[1,5-a][1,3,5]triazin-4-yl)-dimethylamine In an analogous manner to that described in Example 123 b), from 8-benzenesulphonyl-2-methyl-7-methylsulphanyl-3H-pyrazolo[1,5-a][1,3,5]triazin-4-one and dimethylamine there was obtained (8-benzenesulphonyl-2-methyl-7-methylsulphanyl-pyrazolo[1,5-a]-[1,3,5]triazin-4-yl)-dimethylamine as pale pink colored crystals, m.p. 228–230°.

EXAMPLE 127

(8-Benzenesulphonyl-2-methyl-7-methylsulphanyl-pyrazolo[1,5-a][1,3,5]triazin-4-yl)-N',N'-dimethyl-propan-1,3-diamine In an analogous manner to that described in Example 123 b), from 8-benzenesulphonyl-2-methyl-7-methylsulphanyl-3H-pyrazolo[1,5-a][1,3,5]triazin-4-one and 3-dimethylamino-1-propylamine there was obtained (8-benzenesulphonyl-2-methyl-7-methylsulphanyl-pyrazolo[1,5-a][1,3,5]triazin-4-yl)-N',N'-dimethyl-propan-1,3-diamine which was converted with HCl/diethyl ether into the corresponding hydrochloride (1:1.75), m.p. 249–250°.

EXAMPLE 128

8-Benzenesulphonyl-2-methyl-4-(4-methylpiperazin-1-yl)-7-methylsulphanyl-pyrazolo[1,5-a][1,3,5]triazine In an analogous manner to that described in Example 123 b), from 8-benzenesulphonyl-2-methyl-7-methylsulphanyl-3H-pyrazolo[1,5-a][1,3,5]triazin-4-one and 1-methyl-pipazine there was obtained 8-benzenesulphonyl-2-methyl-4-(4-methyl-piperazin-1-yl)-7-methylsulphanyl-pyrazolo[1,5-a][1,3,5]triazine as yellow crystals, m.p. 169–171°.

EXAMPLE 129

8-Benzenesulphonyl-2-methyl-4-(4-benzylpiperazin-1-yl)-7-methylsulphanyl-pyrazolo[1,5-a][1,3,5]triazine In an analogous manner to that described in Example 123 b), from 8-benzenesulphonyl-2-methyl-7-methylsulphanyl- 3H-pyrazolo[1,5-a][1,3,5]triazin-4-one and 1-benzyl there was obtained 8-benzenesulphonyl-2-methyl-4-(4-benzylpiperazin-1-yl)-7-methylsulphanyl-pyrazolo[1,5-a][1,3,5]triazine as beige crystals, m.p. 190–192°.

EXAMPLE A

Tablets of the following composition are produced in the usual manner:

|  | mg/tablet |
| --- | --- |
| Active ingredient | 100 |
| Powd. lactose | 95 |
| White corn starch | 35 |
| Polyvinylpyrrolidone | 8 |
| Na carboxymethlstarch | 10 |
| Magnesium stearate | 2 |
| Tablet weight | 250 |

What is claimed is:

1. Compounds of the general formula

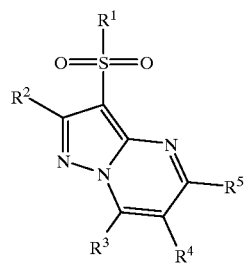

I-A wherein $R^1$ is phenyl, optionally substituted by one or more of lower alkyl, halogen or lower alkoxy; tolyl; pyridyl; naphthyl; or thiophenyl;

$R^2$ is hydrogen; lower alkyl; lower thioalkyl; or hydroxy-lower-alkoxy;

$R^3$ is amino; lower alkylamino; di-lower-alkyl-amino; piperazinyl, optionally substituted by one or more lower alkyl, benzyl, phenyl or hydroxy-lower-alkyl; morpholinyl; imidazolyl; $(CH_3)_2N(CH_2)_nNH—$; $(CH_3)_2N(CH_2)_nO—$ or morpholinyl—$(CH_2)_nO—$in which n signifies 2 or 3;

$R^4$ is hydrogen; lower alkyl; or hydroxy-lower-alkyl;

$R^5$ is hydrogen; halogen; lower alkyl; $C_3$–$C_6$-cycloalkyl; lower alkyl-lower-alkoxy;

hydroxy-lower-alkyl-lower-alkoxy; $(CH_3)_2N(CH_2)_nNH—$; piperazinyl, optionally substituted by lower alkyl; methyl-piperazinyl, optionally substituted by lower alkyl; morpholinyl; methyl-morpholinyl: di-lower-alkylamino; or di-lower-alkylamino-lower-alkyl; or $R^4$ and $R^5$ together represent —$(CH_2)_m$— or —$CH_2$—S—$CH_2$—wherein m is 3 or 4, and their pharmaceutically acceptable salts.

2. Compounds of general formula I-A in accordance with claim 1, wherein $R^3$ is amino.

3. Compound in accordance with claim 2 selected from the group consisting of 3-benzenesulphonyl-5-methyl-2-methylsulphanyl-pyrazolo[1,5-a]pyrimidin-7-ylamine, 3-(4-isopropyl-benzenesulphonyl)-5-methyl-2-methylsulphanyl-pyrazolo[1,5-a]-pyrimidin-7-ylamine, 5-methyl-2-methylsulphanyl-3-(naphthalene-2-sulphonyl)-pyrazolo[1,5-a]-pyrimidin-7-ylamine, 3-(4-fluoro-benzenesulphonyl)-5-methyl-2-methylsulphanyl-pyrazolo[1,5-a]-pyrimidin-7-ylamine, 3-benzenesulphonyl-5-cyclopropyl-2-methylsulphanyl-pyrazolo[1,5-a]pyrimidin-7-ylamine, 3-benzenesulphonyl-2-methylsulphanyl-6,7-dihydro-5H-cyclopenta[d]pyrazolo[1,5-a]pyrimidin-8-ylamine, 3-benzenesulphonyl-5-isopropyl-2-methylsulphanyl-pyrazolo[1,5-a]pyrimidin-7-ylamine, 5-methyl-2-methylsulphanyl-3-(toluene-2-sulphonyl)-pyrazolo[1,5-a]pyrimidin-7-ylamine, 5-methyl-2-methylsulphanyl-3-(toluene-3-sulphonyl)-pyrazolo[1,5-a]pyrimidin-7-ylamine, 3-benzenesulphonyl-5-methoxymethyl-2-methylsulphanyl-pyrazolo[1,5-a]-pyrimidin-6-ylamine, 3-benzenesulphonyl-N5,N5-dimethyl-2-methylsulphanyl-pyrazolo[1,5-a]pyrimidine-5,7-diamine, 3-benzenesulphonyl-N5-(2-dimethylamino-ethyl)-2-methylsulphanyl-pyrazolo[1,5-a]pyrimidine-5,7-diamine, 3-benzenesulphonyl-5-(4-methyl-piperazin-1-yl)-2-methylsulphanyl-pyrazolo[1,5-a]pyrimidin-7-ylamine and 3-benzenesulphonyl-5-dimethylaminomethyl-2-methylsulphanyl-pyrazolo[1,5-a]pyrimidin-7-ylamine.

4. Compounds of general formula I-A in accordance with claim 1, wherein $R^3$ is piperazinyl.

5. Compound in accordance with claim 4 selected from the group consisting of 3-benzenesulphonyl-5-methyl-2-methylsulphanyl-7-piperazin-1-yl-pyrazolo[1,5-a]-pyrimidine, 3-(4-tert-butyl-benzenesulphonyl)-5-methyl-2-methylsulphanyl-7-piperazin-1-yl-pyrazolo[1,5-a]pyrimidine, 3-benzenesulphonyl-5,6-dimethyl-2-methylsulphanyl-7-piperazin-1-yl-pyrazolo[1,5-a]pyrimidine, 3-benzenesulphonyl-2-methylsulphanyl-7-piperazin-1-yl-5-propyl-pyrazolo[1,5-a]-pyrimidine, 3-benzenesulphonyl-5-cyclopropyl-2-methylsulphanyl-7-piperazin-1-yl-pyrazolo[1,5-a]pyrimidine, 3-benzenesulphonyl-2-methylsulphanyl-8-piperazin-1-yl-6,7-dihydro-5H-cyclopenta[d]pyrazolo[1,5-a]pyrimidine, 3-benzenesulphonyl-2-methylsulphanyl-8-piperazin-1-yl-5H,7H-pyrazolo[1,5-a]-thieno[3,4-d]pyrimidine, 5-methyl-2-methylsulphanyl-7-piperazin-1-yl-3-(thiophene-2-sulphonyl)-pyrazolo-[1,5-a]pyrimidine, 3-benzenesulphonyl-2-ethyl-8-piperazin-1-yl-6,7-dihydro-5H-cyclopenta[d]-pyrazolo[1,5-a]pyrimidine and 5-methyl-2-methylsulphanyl-7-piperazin-1-yl-3-(toluene-2-sulphonyl)-pyrazolo[1,5-a]pyrimidine.

6. Compound of general formula I-A in accordance with claim 1, wherein $R^3$ is methylpiperazinyl.

7. Compound in accordance with claim 6 selected from the group consisting of 3-benzenesulphonyl-5-cyclopropyl-2-methylsulphanyl-7-(4-methyl-pipazin-1-yl)-pyrazolo[1,5-a]pyrimidine, 3-benzenesulphonyl-8-(4-methyl-piperazin-1-yl)-2-methylsulphanyl-6,7-dihydro-5H-cyclopenta[d]pyrazolo[1,5-a]pyrimidine, 3-benzenesulphonyl-8-(4-methyl-piperazin-1-yl)-2-methylsulphanyl-5H,7H-pyrazolo[1,5-a]thieno[3,4-d]pyrimidine, 3-benzenesulphonyl-5-isopropyl-7-(4-methyl-piperazin-1-yl)-2-methylsulphanyl-pyrazolo[1,5-a]pyrimidine and 2-[3-benzenesulphonyl-7-(4-methyl-piperazin-1-yl)-2-methylsulphanyl-pyrazolo-[1,5-a]pyrimidine-5-yloxy]-ethanol.

8. A pharmaceutical composition comprising a compound of formula I-A according to claim 1 and a therapeutically inert carrier.

9. Compounds of the general formula

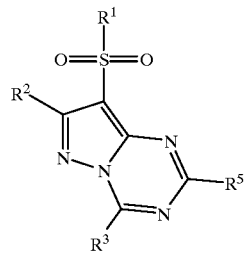

I-B wherein $R^1$ is phenyl, optionally substituted by one or more lower alkyl, halogen or lower alkoxy; tolyl; pyridyl; naphthyl; or thiophenyl;

$R^2$ is hydrogen; lower alkyl; lower thioalkyl; or hydroxy-lower-alkoxy;

$R^3$ is amino; lower alkylamino; di-lower-alkyl-amino; piperazinyl, optionally substituted by one or more lower alkyl, benzyl, phenyl or hydroxy-lower-alkyl; morpholinyl; imidazolyl; $(CH_3)_2N(CH_2)_nNH-$; $(CH_3)_2N(CH_2)_nO-$ or morpholinyl—$(CH_2)_n)O-$—in which n signifies 2 or 3;

$R^5$ is hydrogen; halogen; lower alkyl; $C_3$–$C_6$-cycloalkyl; lower alkyl-lower-alkoxy; hydroxy-lower-alkyl-lower-alkoxy; $(CH_3)_2N(CH_2)_nNH-$; piperazinyl, optionally substituted by lower alkyl; methyl-piperazinyl, optionally substituted by lower alkyl; morpholinyl; methyl-morpholinyl; di-lower-alkylamino; or di-lower-alkylamino-lower-alkyl;

and their pharmaceutically acceptable salts.

10. Compounds of general formula I-B in accordance with claim 9, wherein $R^3$ is amino or methylpiperazinyl.

11. Compound in accordance with claim 10 selected from the group consisting of 8-benzenesulphonyl-7-methylsulphanyl-pyrazolo[1,5-a][1,3,5]triazin-4-ylamine and 8-benzenesulphonyl-2-methyl-4-(4-methylpiperazin-1-yl)-7-methylsulphanyl-pyrazolo[1,5-a][1,3,5]triazine.

12. A pharmaceutical composition comprising a compound of formula I-B according to claim 9, and a therapeutically inert carrier.

* * * * *